(12) United States Patent
Godzich Elakkad et al.

(10) Patent No.: US 11,432,951 B2
(45) Date of Patent: Sep. 6, 2022

(54) TOOLS FOR TRANSURETHRAL DEPLOYMENT AND FIXATION OF GRAFT FOR THE MANAGEMENT AND TREATMENT OF URETHRAL STRICTURES

(71) Applicant: THE JOHNS HOPKINS UNIVERSITY, Baltimore, MD (US)

(72) Inventors: Chanya Godzich Elakkad, Baltimore, MD (US); Teja Maruvada, Baltimore, MD (US); Joseph A. Pia, Baltimore, MD (US); Shravya Srigiri, Minneapolis, MN (US); Kendall Covington, Baltimore, MD (US); Edward James Wright, Severna Park, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 16/346,220

(22) PCT Filed: Oct. 31, 2017

(86) PCT No.: PCT/US2017/059205
§ 371 (c)(1),
(2) Date: Apr. 30, 2019

(87) PCT Pub. No.: WO2018/081776
PCT Pub. Date: May 3, 2018

(65) Prior Publication Data
US 2020/0046529 A1 Feb. 13, 2020

Related U.S. Application Data

(60) Provisional application No. 62/414,875, filed on Oct. 31, 2016.

(51) Int. Cl.
*A61F 2/95* (2013.01)
*A61F 2/04* (2013.01)

(52) U.S. Cl.
CPC .............. *A61F 2/95* (2013.01); *A61F 2/04* (2013.01); *A61F 2002/047* (2013.01)

(58) Field of Classification Search
CPC ........ A61F 2002/047; A61F 2/04; A61F 2/95; A61L 2400/10
See application file for complete search history.

(56) References Cited

U.S. PATENT DOCUMENTS 4,250,873 A 2/1981 Bonnet
4,773,400 A 9/1988 Borodulin et al.
(Continued)

FOREIGN PATENT DOCUMENTS

EP      2982347 A2    2/2016
WO   2012123950 A2   9/2012
WO   2018081776 A1   5/2018

OTHER PUBLICATIONS

Akkoc, A., et al., "Use and outcomes of amplatz renal dilator for treatment of urethral strictures", Int Braz J Urol, 2016, vol. 42, No. 2: pp. 356-364.
(Continued)

*Primary Examiner* — Brooke Nicole Labranche
(74) *Attorney, Agent, or Firm* — Harrity & Harrity, LLP

(57) ABSTRACT

An embodiment in accordance with the present invention provides a device and method for the treatment of urethral stricture. The present invention places and holds a graft at an incised urethral stricture site for 5-21 days, while the graft adherences to the incised urethral stricture site. A device of the present invention includes a delivery component, a graft carrier component, and a removal component. In some embodiments, the delivery and removal components may be combined into the same device. The delivery component, the
(Continued)

graft carrier component, and the removal component are all configured to enter and exit the urethra without trauma. A method according to an embodiment of the present invention includes harvesting a graft, loading the graft onto the graft carrier component, introducing the delivery device into the urethra with the graft carrier component and graft loaded, and delivering of the graft to the incised urethral stricture site.

24 Claims, 45 Drawing Sheets

(56) References Cited

U.S. PATENT DOCUMENTS

| | | | |
|---|---|---|---|
| 5,108,416 A | 4/1992 | Ryan et al. | |
| 5,322,501 A | 6/1994 | Mahmud-Durrani | |
| 5,391,196 A | 2/1995 | Devonec | |
| 5,746,745 A | 5/1998 | Abele | |
| 6,221,081 B1 | 4/2001 | Milkus et al. | |
| 7,011,674 B2 | 3/2006 | Brenneman | |
| 10,076,644 B2 | 9/2018 | Kaisha | |
| 2002/0007206 A1* | 1/2002 | Bui | A61F 2/962 623/1.11 |
| 2004/0078088 A1 | 4/2004 | Gellman | |
| 2005/0154443 A1 | 7/2005 | Linder et al. | |
| 2006/0047336 A1 | 3/2006 | Gale et al. | |
| 2010/0049295 A1* | 2/2010 | Satasiya | A61F 2/95 623/1.11 |
| 2013/0310913 A1 | 11/2013 | Wang et al. | |
| 2015/0216609 A1 | 8/2015 | Arastoo et al. | |
| 2015/0328027 A1 | 11/2015 | Nishio et al. | |
| 2016/0045300 A1 | 2/2016 | Kaisha | |
| 2016/0045302 A1* | 2/2016 | Nishio | A61F 2/042 623/23.66 |
| 2016/0089169 A1* | 3/2016 | Nishio | A61B 17/22 606/194 |
| 2016/0243341 A1* | 8/2016 | Nishio | A61F 2/958 |

OTHER PUBLICATIONS

Bansal, A., et al., "Early removal of urinary catheter after excision and primary anastomosis in anterior urethral stricture", Turkish Journal of Urology, 2016, vol. 42, No. 2: pp. 80-83.
Wolf, J., et al., "Surgical techniques: endoscopic and percutaneous procedures", Emergencies in Urology, Springer, 2007, Chapter 19, pp. 486-487.
Pettersson, et al., Endourethral Urethroplasty: A Simple Method for Treatment of Urethral Strictures by Internal Urethrotomy and Primary Split Skin Grafting. Br J Urol. Jun. 1978;50(4):257-61.
Naude, et al.. Endoscopic skingraft urethroplasty. World J Urol. 1998; 16(3): 171-4.
Oosterlinck, et al.. Endoscopic Urethroplasty with a Free Graft on a Biodegradable Polyglycolic Acid Spiral Stent. Eur Urol. Jan. 2000;37(1):112-5.
Le Roux, et al., Endoscopic urethroplasty with unseeded small intestinal submucosa collagen matrix grafts: a pilot study. J Urol. Jan. 2005; 173(1): 140-3.
Alwaal, et al., Epidemiology of urethral strictures. Transl Androl Urol. Jun. 2014; 3(2): 209-213.
Santucci, et al., Male urethral stricture disease. J Urol. May 2007; 177(5):1667-74.
Anger, et al., The morbidity of urethral stricture disease among male medicare beneficiaries. BMC Urol. 2010; 10: 3.
Djordjevic, et al., Treatment of Urethral Stricture Disease by Internal Urethrotomy, Dilation, or Stenting. Eur Ur Supp. Jan. 2016; 15(1): 7-12.
Lazzeri, et al., Incidence, Causes, and Complications of Urethral Stricture Disease. Eur Ur Supp. Jan. 2016; 15(1) 2-6.
Engel, et al., Reconstructive Management with Urethroplasty. Eur Ur Supp. Jan. 2016; 15(1): 13-16.
Extended European Search Report dated Jun. 19, 2020, for EP application 17864126.2.

\* cited by examiner

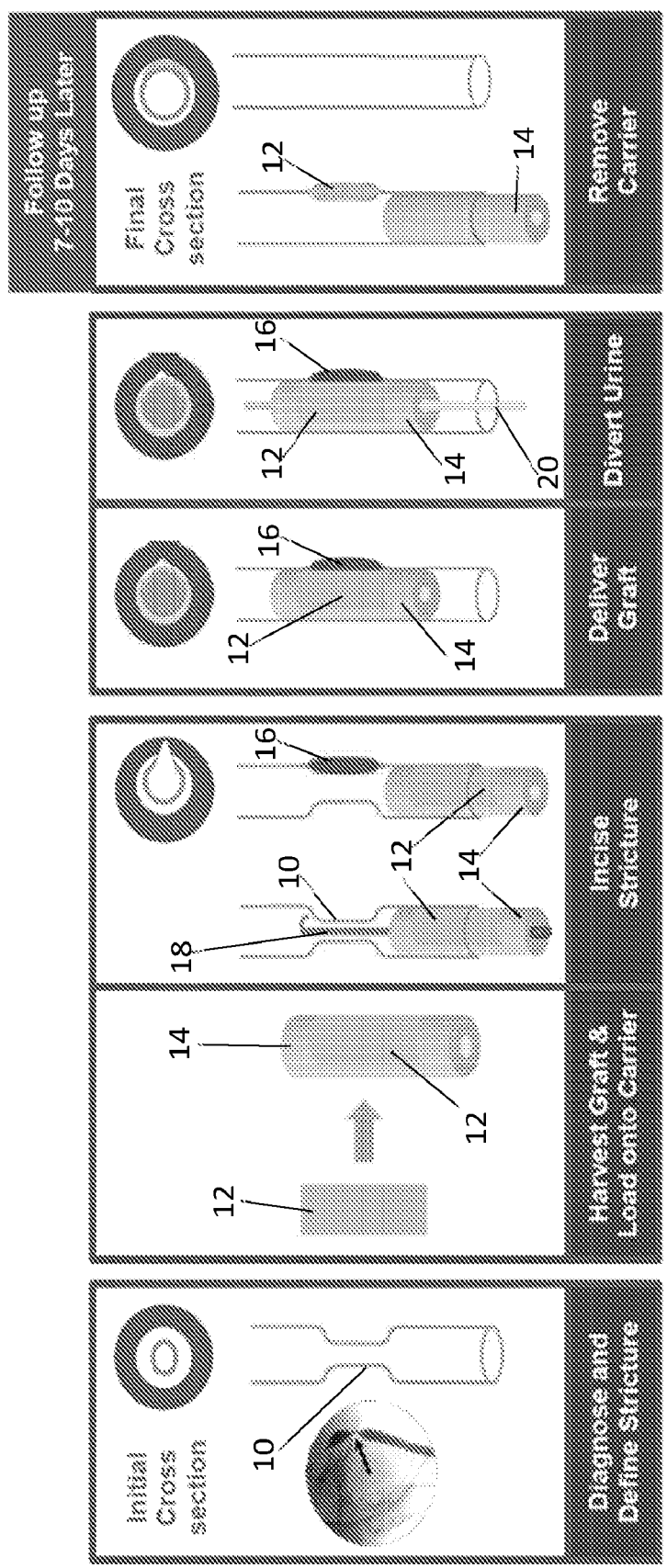

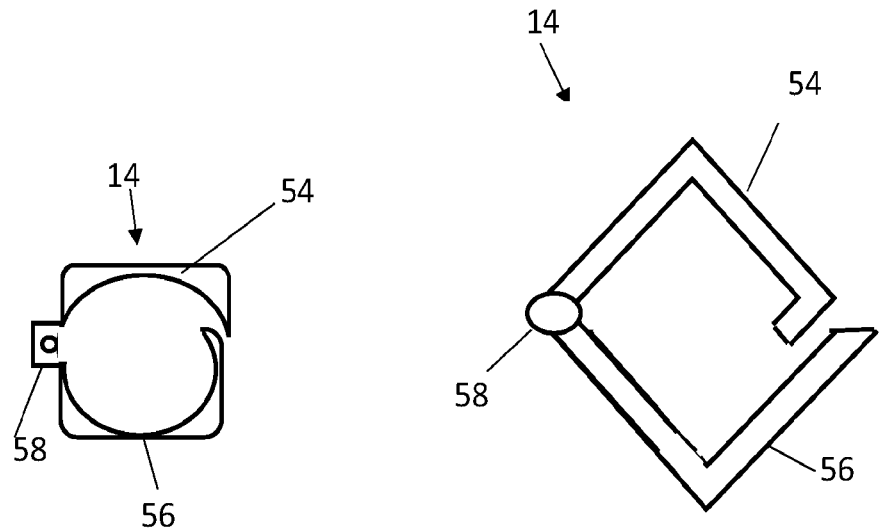
FIG. 12A
FIG. 12B
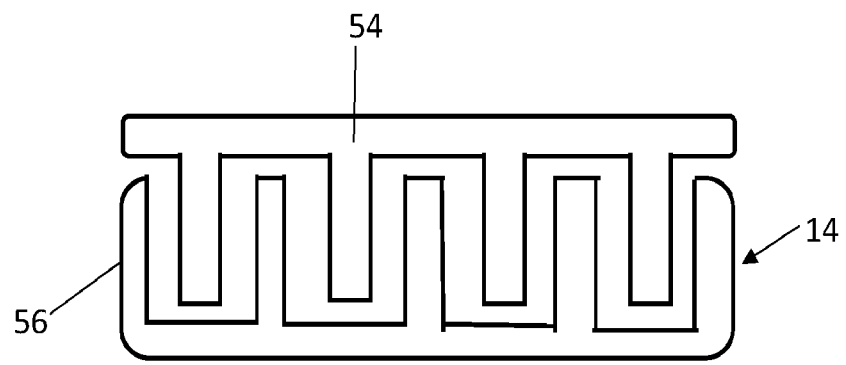
FIG. 12C

TOOLS FOR TRANSURETHRAL DEPLOYMENT AND FIXATION OF GRAFT FOR THE MANAGEMENT AND TREATMENT OF URETHRAL STRICTURES

CROSS-REFERENCE TO RELATED APPLICATIONS

This application is a 35 U.S.C. § 371 U.S. national entry of International Application PCT/US2017/059205, having an international filing date of Oct. 31, 2017, which claims the benefit of U.S. Provisional Application No. 62/414,875, filed Oct. 31, 2016, the content of each of the aforementioned applications is herein incorporated by reference in their entirety.

GOVERNMENT RIGHTS

This invention was made with government support under grant number 1640778 awarded by the National Science Foundation. The government has certain rights in the invention.

FIELD OF THE INVENTION

The present invention relates generally to medical devices. More particularly, the present invention relates to methods and tools for the management and treatment of urethral strictures, comprising transurethral deployment and fixation of a graft.

BACKGROUND OF THE INVENTION

Urethral strictures are a fibrotic narrowing of the urethra, which act like a band of scar tissue, resulting in painful and frequent urination, and difficulty voiding. This condition occurs primarily in men, and severely affects their quality of life. It affects men of all ages, but increases in incidence with age. In the United States, the reported utilization of urethral stricture treatment is 0.9% in the Medicare male population.

The bulbar urethra is the most common region of urethral structure—it lies between the bladder neck and the penile-scrotal junction, which leads to the pendulous (or penile) urethra. Diagnosis is done by cystoscopy or by x-ray with contrast fluid. The most common location of stricture is the bulbar urethra (internal). While the cause is unknown for some (idiopathic), others are caused by saddle injury, infection, catheterization or trauma. In addition to idiopathic stricture (cause unknown) urethral catheterization, saddle injury, urinary tract infection, and radiation can cause the urothelium and the underlying corpus spongiosum to scar. This scarring is characterized by a reduction in lumen diameter, which occurs when the spongy elastic tissue surrounding the urethra is transformed into a hard and inflexible tissue through the deposition of collagen—ultimately resulting in a urethral stricture.

Existing treatment options fall into two categories. The first is a category of minimally invasive approaches to widen the urethra which are relatively simple to perform, such as dilation and urethrotomy. These involve stretching the stricture, or cutting the scar with a laser, cold knife, or hot knife. Unfortunately these procedures are highly ineffective, with success rates as low as 9%. The second is a category of highly effective surgical urethral reconstruction (anastomotic urethroplasty and substitution urethroplasty). The substitution urethroplasty currently consists of an open surgery with a perineal incision, excision of scar tissue, and placement of an autologous graft harvested. This technique provides new epithelium which promotes healthy healing and increases the lumen diameter of the urethra. While a highly effective treatment option, with success rates of around 86%, the invasive nature of this surgery increases the potential for complications such as erectile dysfunction and fistula formation. Moreover, only 4.2% of urologists feel comfortable performing a substitution urethroplasty due its complexity, which are performed almost exclusively by fellowship trained reconstructive urologists.

The clinical care pathway typically begins with a minimally invasive treatment, and suggests substitution urethroplasty if patients experience a recurrence. However, many undergo repeat ineffective minimally invasive treatments to avoid the extended recovery period, and the risks associated with these long complex open surgical procedures. This repetitive treatment cycle aggravates the patient's condition and is economically inefficient for both the patient and the healthcare system. General urologists have no durable treatment option to offer patients, aside from referral to a reconstructive urologist for surgery. There is a gap that exists between minimally invasive and minimally effective treatments, and effective surgical intervention, and the need for an innovation to bridge this gap.

Prior attempts at minimally invasive (endoscopic) urethroplasty were clinically successful; however, the design of these initial techniques encompassed several barriers to adoption that prevented them from achieving widespread utilization and impacting patient care. Endoscopic urethroplasties outlined in literature required multiple people to perform as a result of inadequate and complex tooling, which made it significantly more complicated than current minimally invasive procedures. These complex techniques were piloted by reconstructive urologists, and there is a lack of specialized tools which make such approaches accessible to general urologists the frontline care providers for patients with urethral strictures.

Therefore, it would be advantageous to provide a tool for transurethral deployment and fixation of a graft for the management and treatment of urethral strictures, which can be used with the tools and skills accessible to both general urologists and reconstructive urologists.

SUMMARY OF THE INVENTION

The foregoing needs are met, to a great extent, by the present invention, wherein in one aspect a device for the treatment of urethral strictures includes a graft carrier component. The graft carrier component is configured to hold a graft for placement at a urethral stricture site. The graft carrier component is further configured to enter the urethra at a first diameter and expand to a second diameter when placed at the urethral stricture site. The device also includes a delivery component configured to advance the graft carrier component through the urethra, to the urethral stricture site, for graft adherence at the urethral stricture site.

In accordance with another aspect of the present invention, the graft carrier component can include one or more parts. The one or more parts of the graft carrier component can include a locking mechanism for joining the one or more parts into a single part. The device can include platens to hold a graft membrane in place on the graft carrier component. The device also includes a fixation component for fixing the graft carrier component at the urethral stricture site.

In accordance with another aspect of the present invention, a method of treatment of urethral strictures includes securing a graft membrane to a carrier component and coupling the carrier component to a delivery component. The method includes inserting the delivery component with the coupled carrier component into the urethra and incising a stricture site. Additionally, the method includes advancing the carrier component to the stricture site.

In accordance with yet another aspect of the present invention, the method includes inserting an incision tool through a lumen defined by the delivery component. Additionally, the method includes inserting an endoscope for illumination and visualization through a lumen defined by the delivery component. The method includes fixing the carrier component at the stricture site. The method includes locking one or more parts of the carrier component together. The method can also include passing a Foley catheter through a lumen defined by the carrier component. The method includes leaving the carrier component at the stricture site for approximately 5 to 21 days. The method also includes removing the carrier component after graft membrane adherence at the stricture site.

BRIEF DESCRIPTION OF THE DRAWINGS

The accompanying drawings provide visual representations, which will be used to more fully describe the representative embodiments disclosed herein and can be used by those skilled in the art to better understand them and their inherent advantages. In these drawings, like reference numerals identify corresponding elements and:

FIGS. 1A-1F illustrate a schematic view of steps of a method for placing a graft at an incised urethral stricture site, according to an embodiment of the present invention.

FIGS. 12A-12C illustrate another embodiment for a graft carrier component, according to an embodiment of the present invention.

DETAILED DESCRIPTION

Figure 2A:
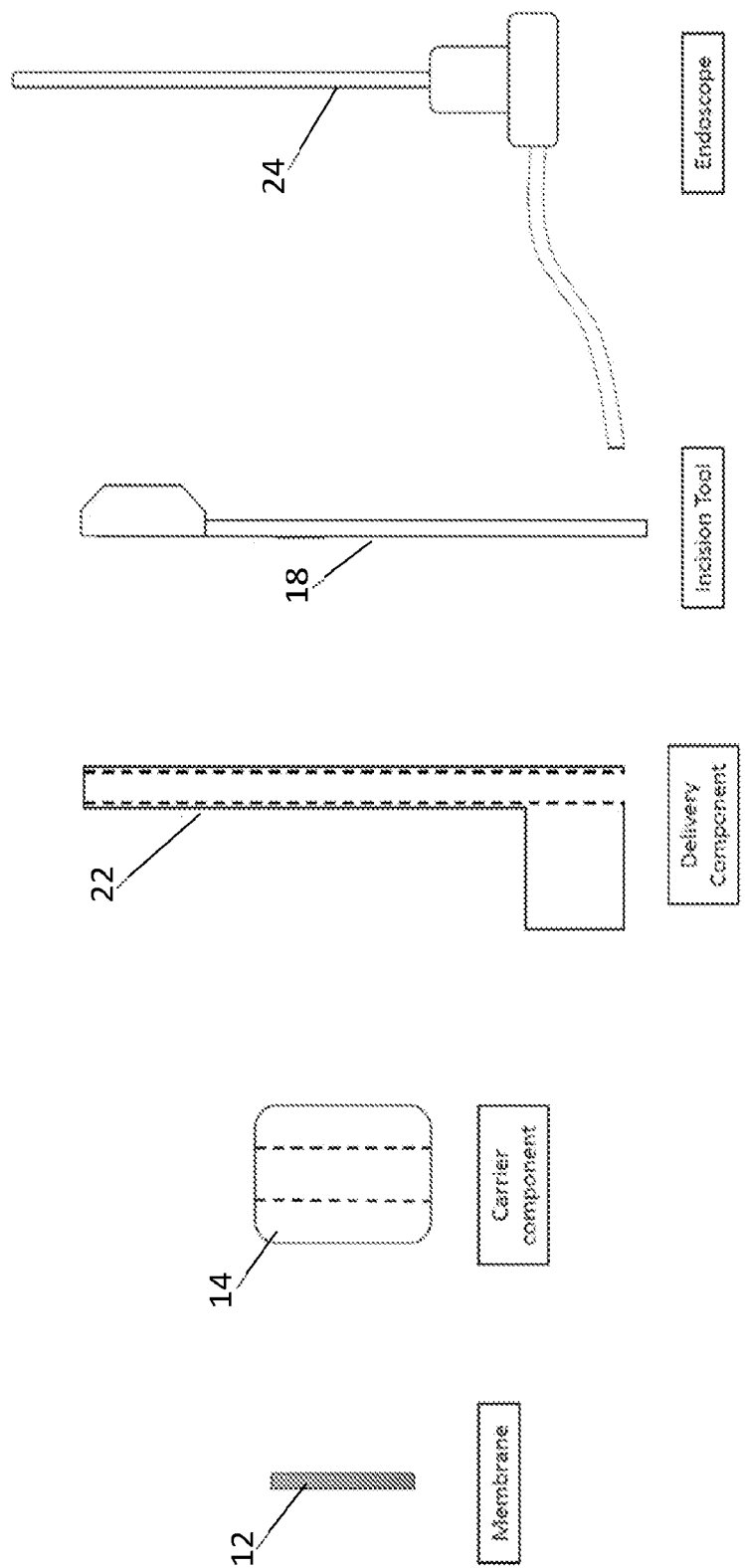
FIGS. 2A-2I illustrate a schematic view of steps of a method for placing a graft at an incised urethral stricture site, according to an embodiment of the present invention.

The presently disclosed subject matter now will be described more fully hereinafter with reference to the accompanying Drawings, in which some, but not all embodiments of the inventions are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Drawings. Therefore, it is to be understood that the presently disclosed subject matter is not to be limited to the specific embodiments disclosed and that modifications and other embodiments are intended to be included within the scope of the appended claims.

An embodiment in accordance with the present invention provides a method and device for the treatment of urethral stricture. The present invention places and holds a graft at an incised urethral stricture site for 5-21 days, while the graft adherences to the incised urethral stricture site. A device of the present invention includes a delivery component, a graft carrier component, and a removal component. In some embodiments, the delivery and removal components may be combined into the same system. The delivery component, the graft carrier component, and the removal component are all configured to enter and exit the urethra without urethral trauma. A method according to an embodiment of the present invention includes harvesting a graft, loading the graft onto the graft carrier component, introducing the delivery component into the urethra with the graft carrier component and graft loaded, and delivering of the graft to the incised urethral stricture site.

FIGS. 1A-1F illustrate a schematic view of steps of a method for placing a graft at an incised urethral stricture site, according to an embodiment of the present invention. A method according to an embodiment of the present invention includes placing a graft at an incised urethral stricture site. As illustrated in FIG. 1A, the urethral stricture site 10 is located, diagnosed, and defined. The graft 12 is harvested and loaded onto a graft carrier component 14, as illustrated in FIG. 1B. The graft 12 can be harvested from the buccal mucosa or any other graft donor site known to or conceivable to one of skill in the art. When the graft 12 is loaded onto the graft carrier component 14 it can be fenestrated or un-fenestrated. As illustrated in FIG. 1C, the stricture site 10 is incised with a tool 18, and as illustrated in FIG. 1D, the graft 12 is delivered to the incised stricture site 16 on the graft carrier component 14. All of these steps are achieved with only one entry into the urethra. The incision of the stricture site 10 can be completed using the delivery component 22 or using traditional tools for stricture incision. The graft 12 can be delivered to the incised stricture site 16 with or without a sheath. It is also possible, that the present invention provides visualization of the stricture site 10 and/or the incised stricture site 16 throughout the procedure, including incision of the stricture site. After delivery of the graft 12 and deployment from the delivery device 22, the graft carrier component 14 can be expanded in order to create a wide enough lumen through the urethra at the stricture site 10. The graft carrier component 14 and/or any expansion and/or fixation systems may or may not be left at or near the urethral stricture site. Urine can be diverted through the graft carrier component 14 through a Foley catheter 20, as illustrated in FIG. 1E. Alternately, fixation of the graft carrier component 14 can be with a fixation component such as barbs that extend from the graft carrier component after placement or sutures that hold the graft carrier component in place, as will be described further herein. After a graft adherence period, the graft carrier component is removed, leaving behind the graft 12, as illustrated in FIG. 1F. The graft adherence period is often between 5 and 10 days, but can be any suitable amount of time known to or conceivable by one of skill in the art.

FIGS. 2A-2I illustrate a schematic view of steps of a method for placing a graft at an incised urethral stricture site, according to an embodiment of the present invention. FIG. 2A illustrates an overview of the components of the device for the execution of the method described with respect to FIGS. 2B-2I. FIG. 2A illustrates a graft membrane 12, which may be harvested from the patient, and a carrier component 14 for delivery of that graft membrane 12 to the desired location. As illustrated in FIG. 2A the carrier component 14 can be formed from a single, non-separable part. A delivery component 22 is used to deliver the carrier component 14 loaded with the graft membrane 12 to the desired location. An incision tool 18 can be used for incising the stricture site before placement of the graft membrane 12. This tool 18 can be included as a component of the present invention and designed specifically for use with the present invention or can be an off the shelf incision tool. Additionally, an endoscope 24 is used for delivery and visualization during the procedure.

Figure 2B:
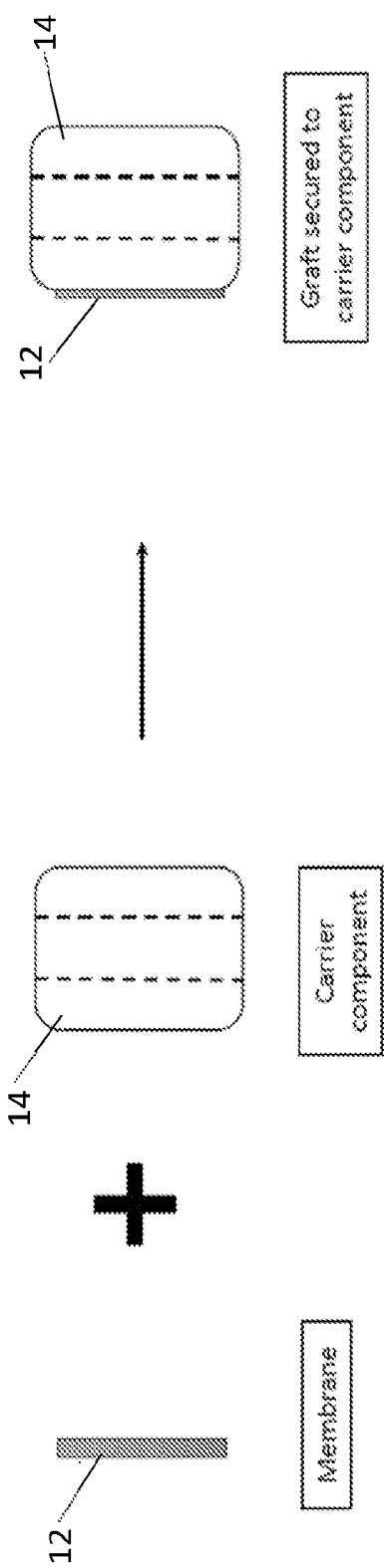
Figure 2C:
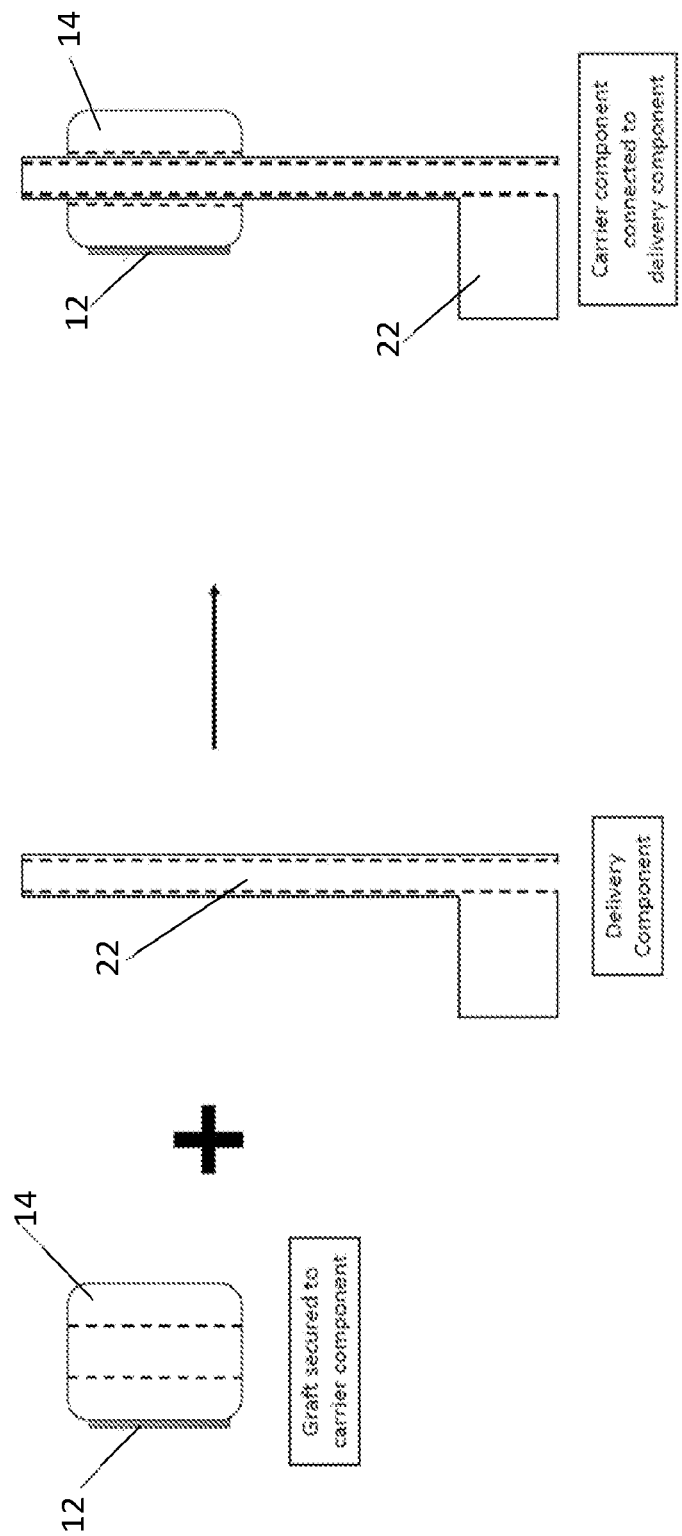
Figure 2D:
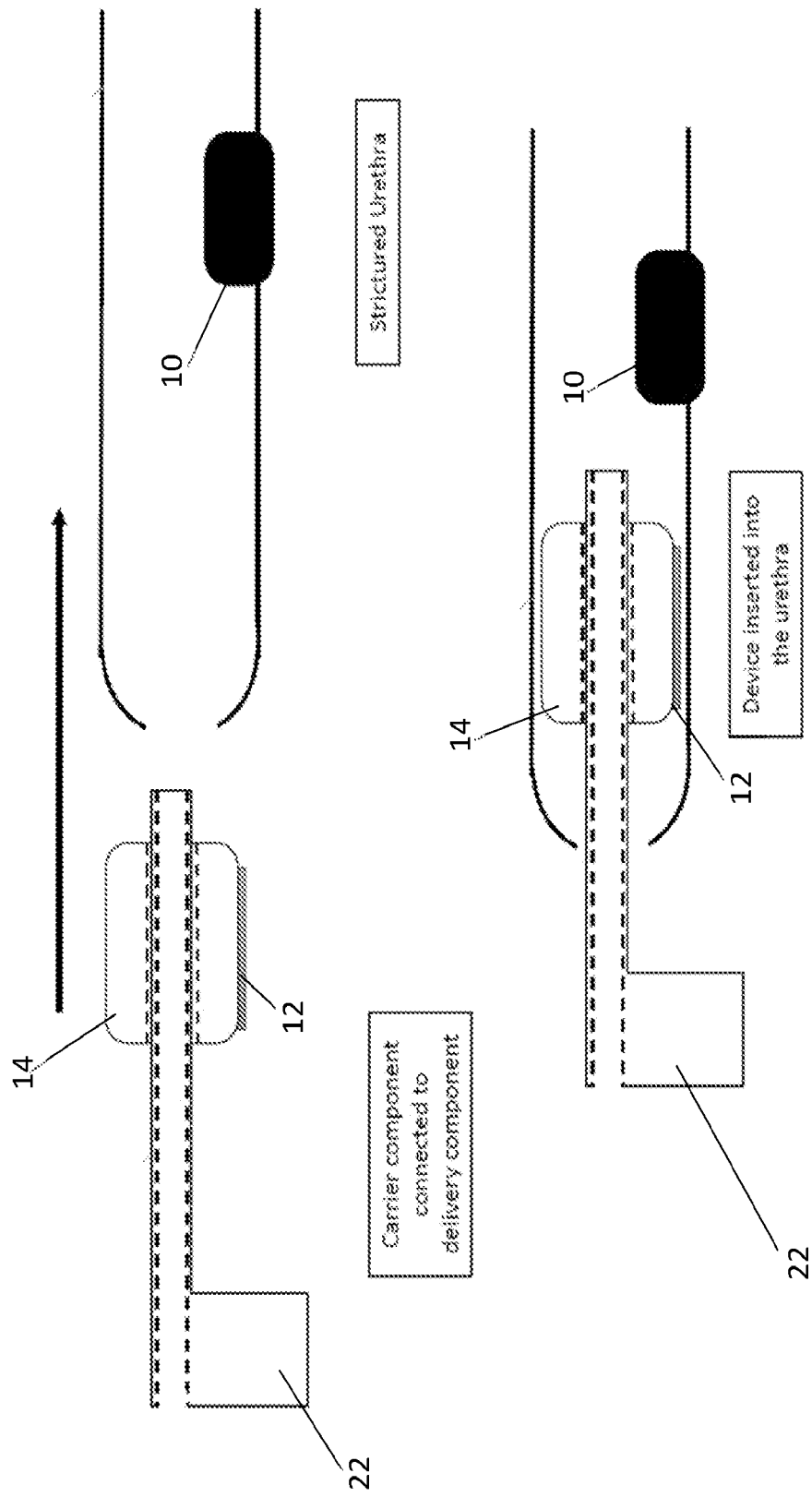

FIG. 2B illustrates a graft membrane 12 being secured on a carrier component 14, according to an embodiment of the present invention. As illustrated in FIG. 2B, the carrier component 14 takes the form of a single, non-separable part. In other embodiments, the carrier component 14 may be two or more separable and attachable parts, as described herein and as would be known to or conceivable to one of skill in the art. Further with respect to FIG. 2B the membrane graft 12 that was harvested for placement at the urethral stricture site is secured to the carrier component 14. FIG. 2C illustrates the carrier component 14 and the secured graft membrane 12 being coupled to the delivery component 22 for delivery to the urethral stricture site 10. FIG. 2D illustrates the carrier component 14 coupled to the delivery component 22, being inserted into the urethra and advanced to the urethral stricture site 10.

Figure 2E:
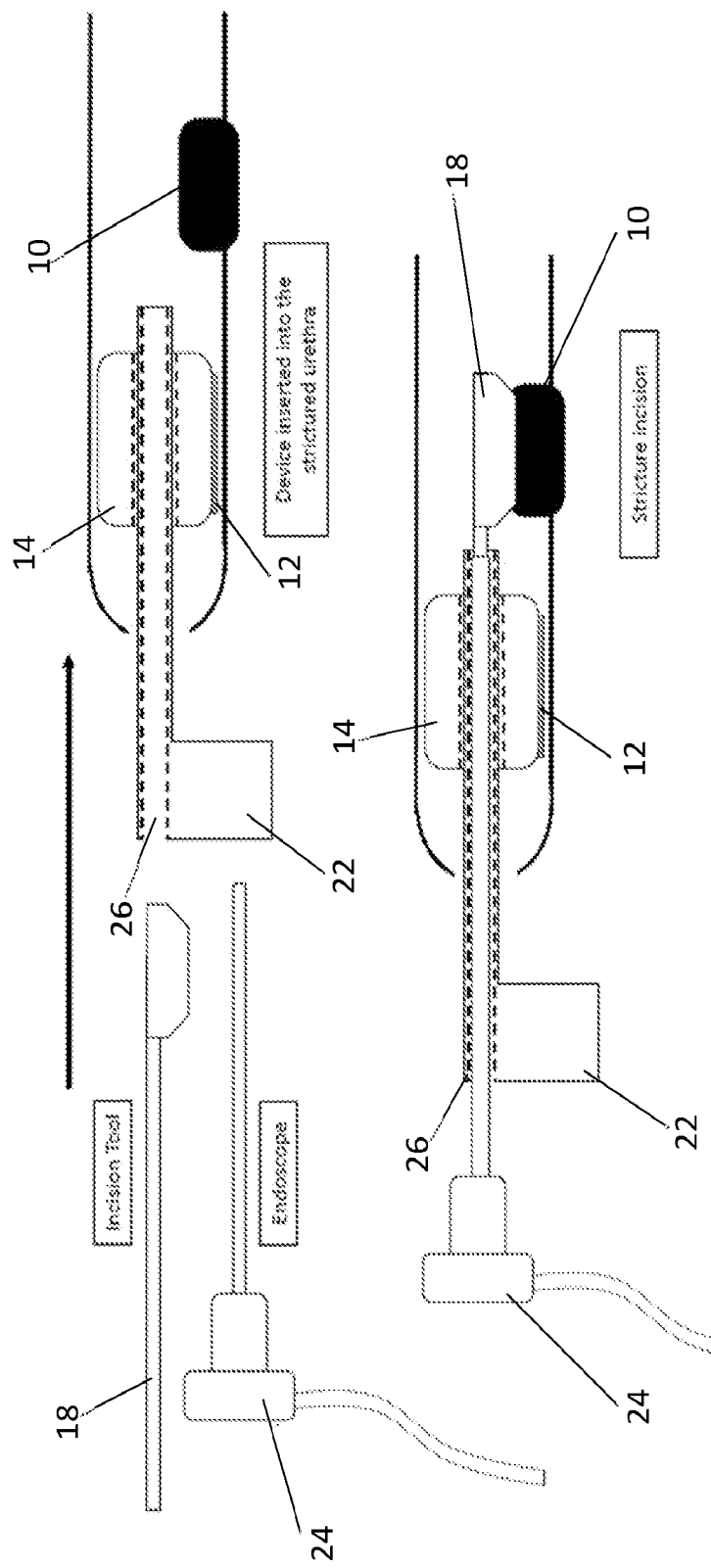
Figure 2F:
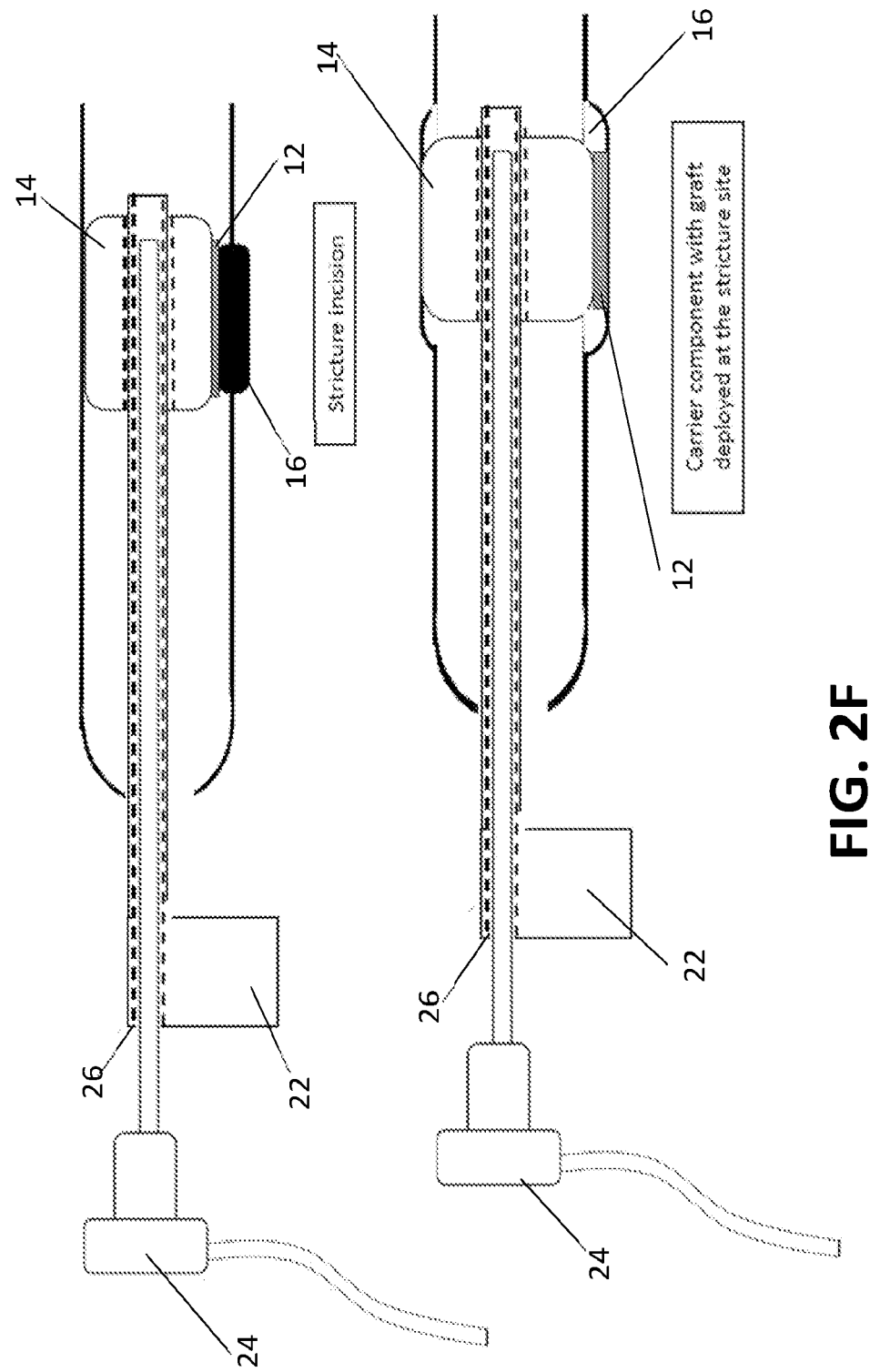

FIG. 2E illustrates an incision tool being inserted through a lumen of the delivery into the strictured urethra. The incision tool 18 is used to incise the stricture site 10 to prepare the stricture site 10 for placement of the graft membrane 12, also illustrated in FIG. 2E. An endoscope 24 is inserted through the lumen 26 of the delivery component 22 to allow for illumination and visualization of the stricture site 10 during incision and also during placement of the graft membrane 12. Further, FIG. 2F illustrates advancement of the carrier component to the incised urethral stricture site 16 and deployment of the carrier component 14 with the graft membrane 12 at the incised stricture site 16. The placement of the carrier component is visualized using the endoscope. As illustrated in FIG. 2F, the carrier component 14 may be fixed in place via expansion of the size of the carrier component. However, it should be noted that fixation can be achieved in a number of ways. The methods of fixation included herein are merely examples and any other suitable form of fixation, known to or conceivable to one of skill in the art could also be used.

Figure 2G:
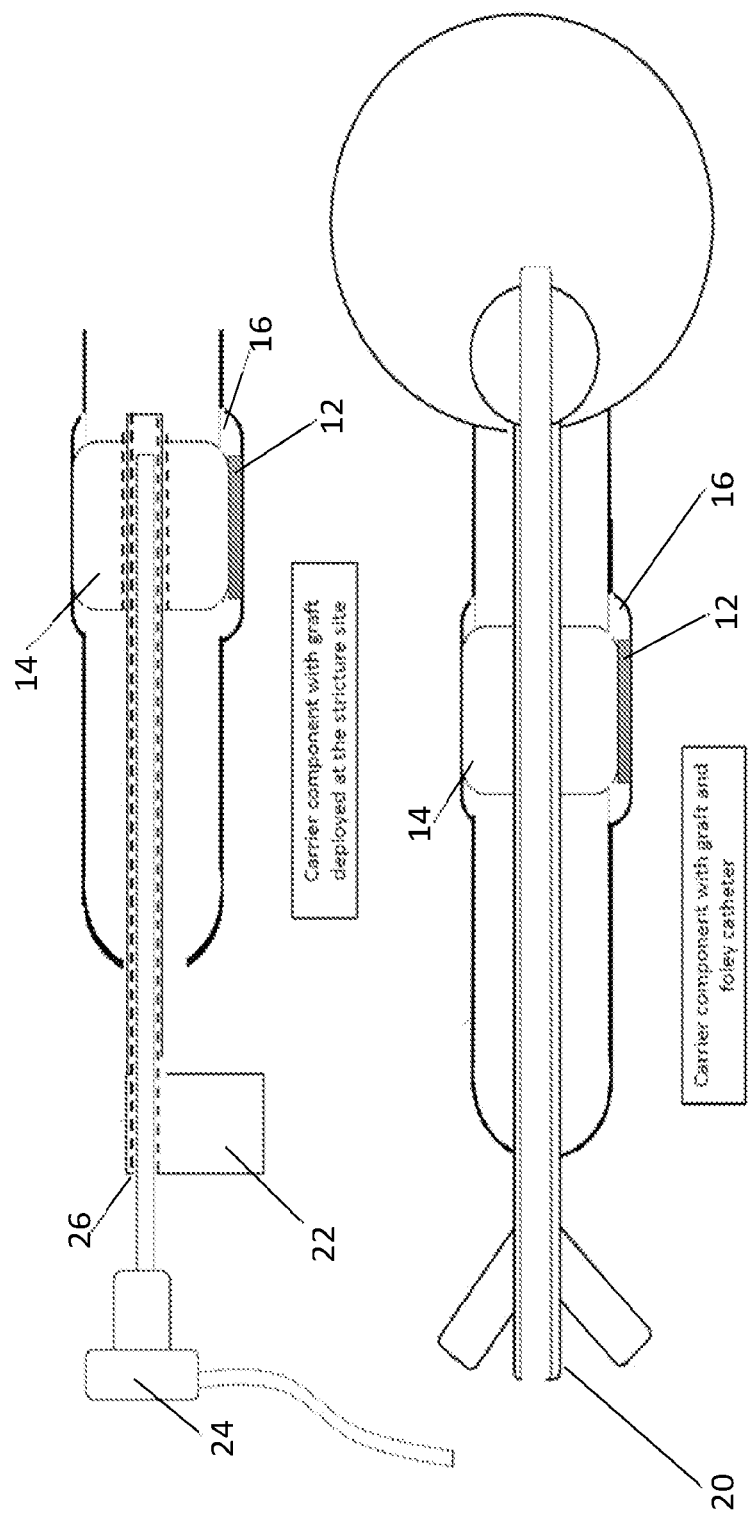
Figure 2H:
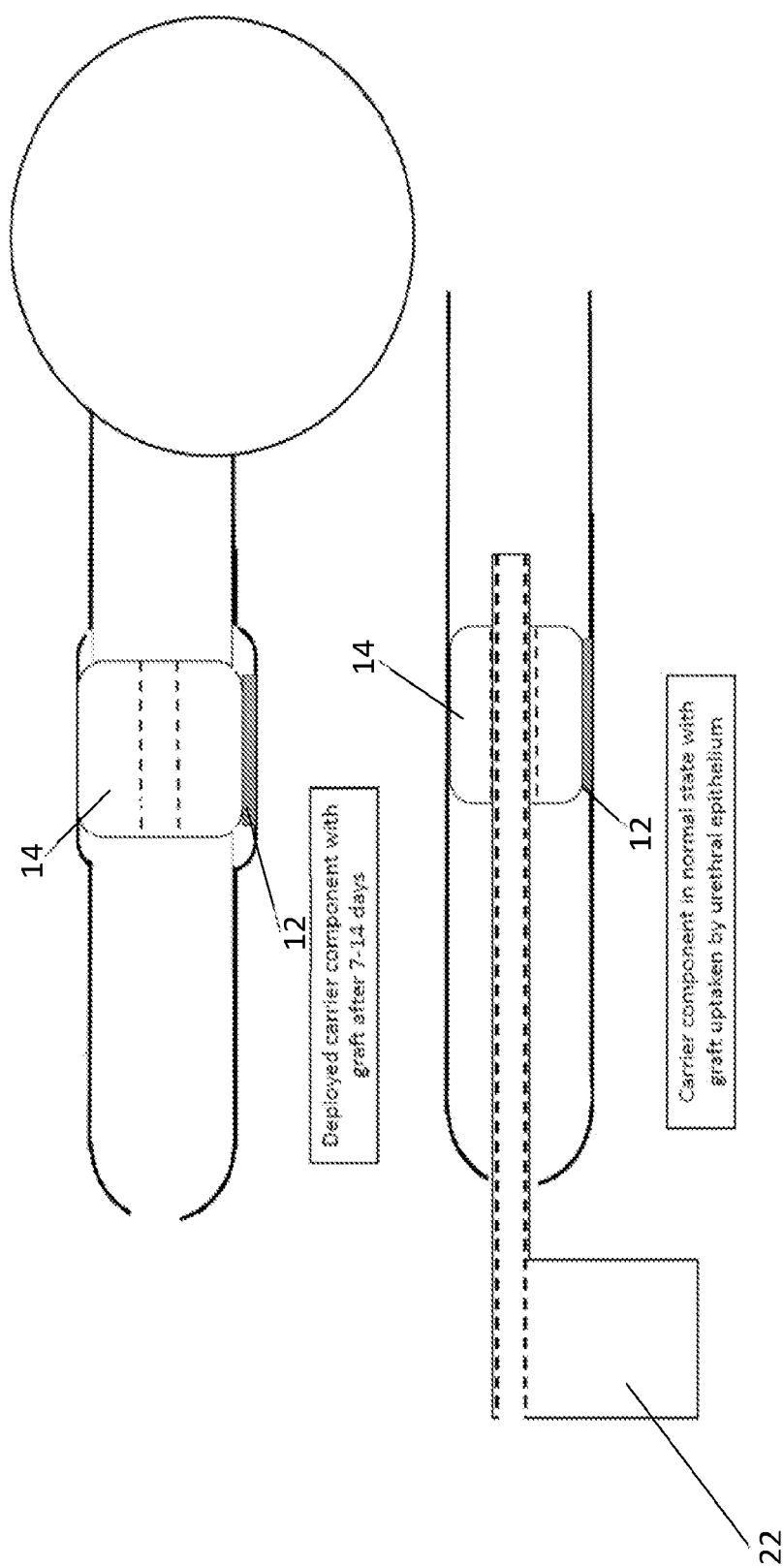
Figure 2I:
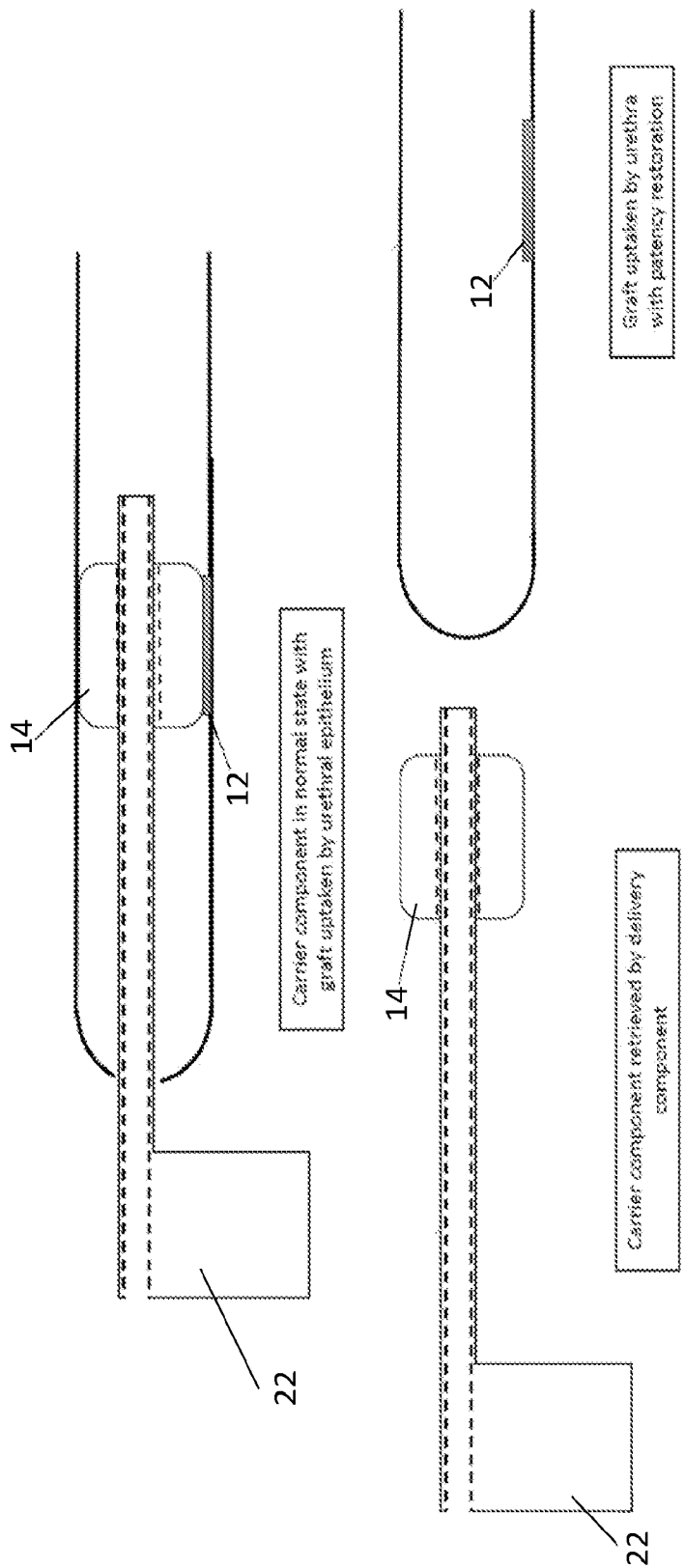

As illustrated in FIG. 2G, the carrier component 14 with the graft membrane 12 is deployed at the incised stricture site 16 and a Foley catheter 20 can then be inserted to allow for the passage of urine during graft adherence. FIG. 2H illustrates the adherence process which can take approximately 7 to 14 days ending with graft adherence to the urethral epithelium. FIG. 2I illustrates the carrier component 14 with the graft membrane 12 adherence to the epithelium complete followed by the carrier component 14 being retrieved by the delivery component 22. It should be noted that the removal of the carrier component can be completed with the delivery component that advanced the carrier component to the urethral stricture site or with a separate removal component configured for the removal of the carrier component. The graft membrane 12 is left behind with urethral patency restored.

Figure 3A:
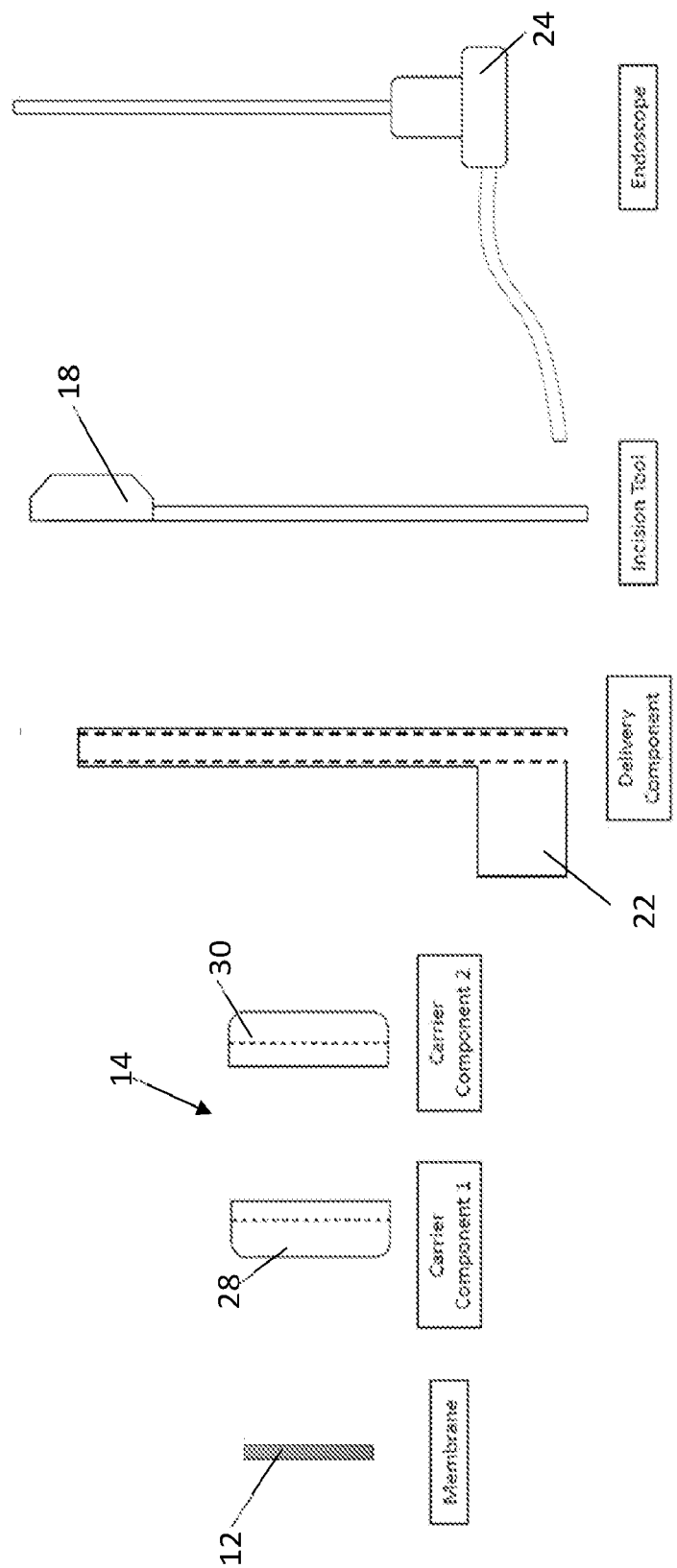
FIGS. 3A-3I illustrate a schematic view of steps of a method for placing a graft at an incised urethral stricture site, according to an embodiment of the present invention.

FIGS. 3A-3I illustrate a schematic view of steps of a method for placing a graft at an incised urethral stricture site, according to an embodiment of the present invention. FIG. 3A illustrates an overview of the components of the device for the execution of the method described with respect to FIGS. 3B-3I. FIG. 3A illustrates a graft membrane 12 harvested from the patient and a carrier component 14 for delivery of that graft membrane 12 to the desired location. As illustrated in FIG. 3A, the carrier component 14 can be formed from two or more detachable and attachable parts 28, 30. A delivery component 22 is used to deliver the carrier component 14 loaded with the graft membrane 12 to the desired location. An incision tool 18 can be used for incising the stricture site 10 before placement of the graft membrane. This tool 18 can be included as a component of the present invention and designed specifically for use with the present invention or can be an off the shelf incision tool. Additionally, an endoscope 24 is used for delivery and visualization during the procedure.

Figure 3B:
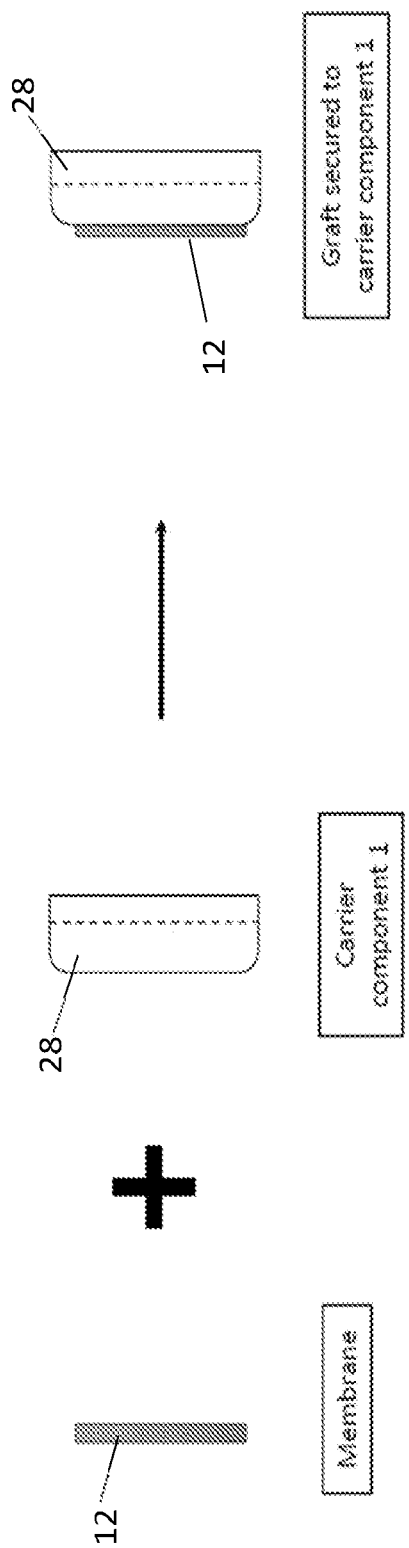
Figure 3C:
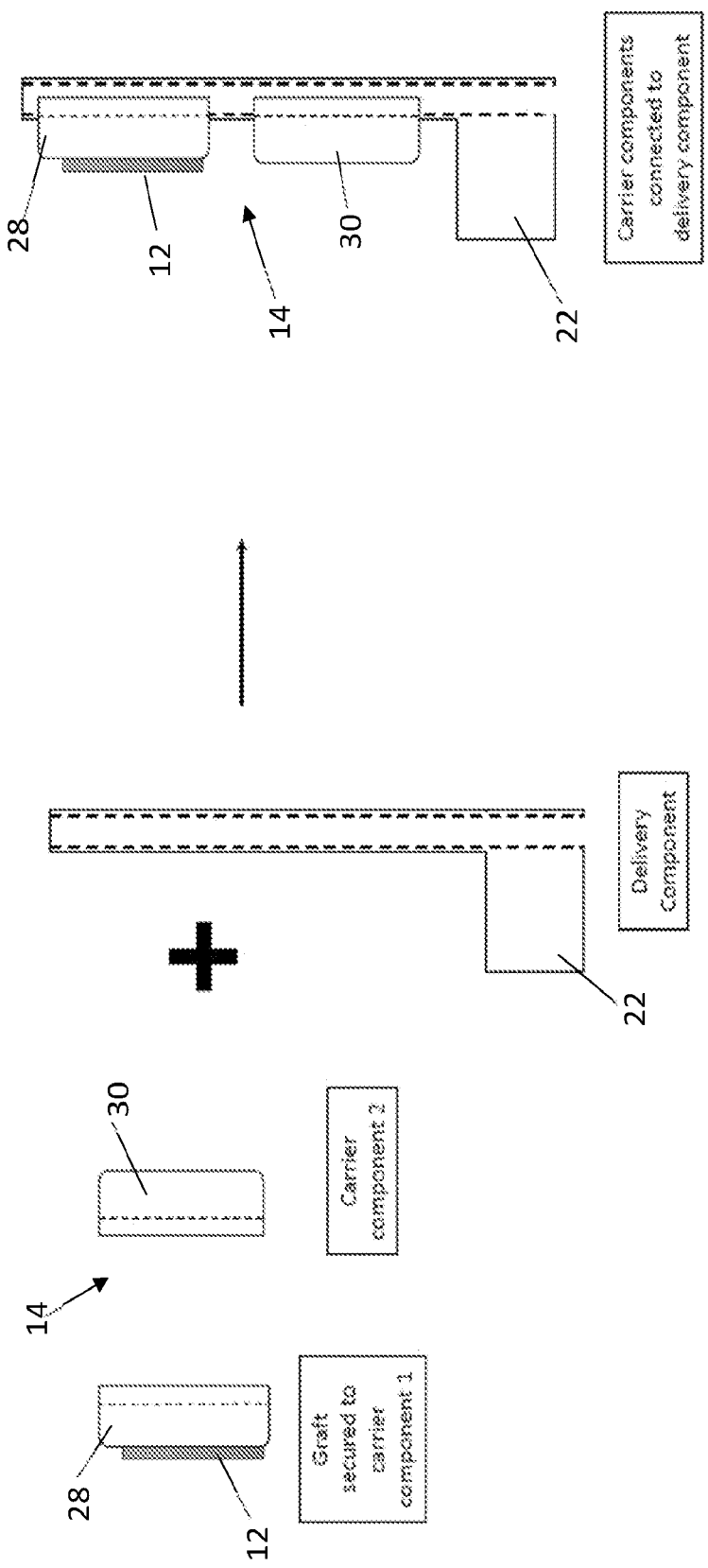
Figure 3D:
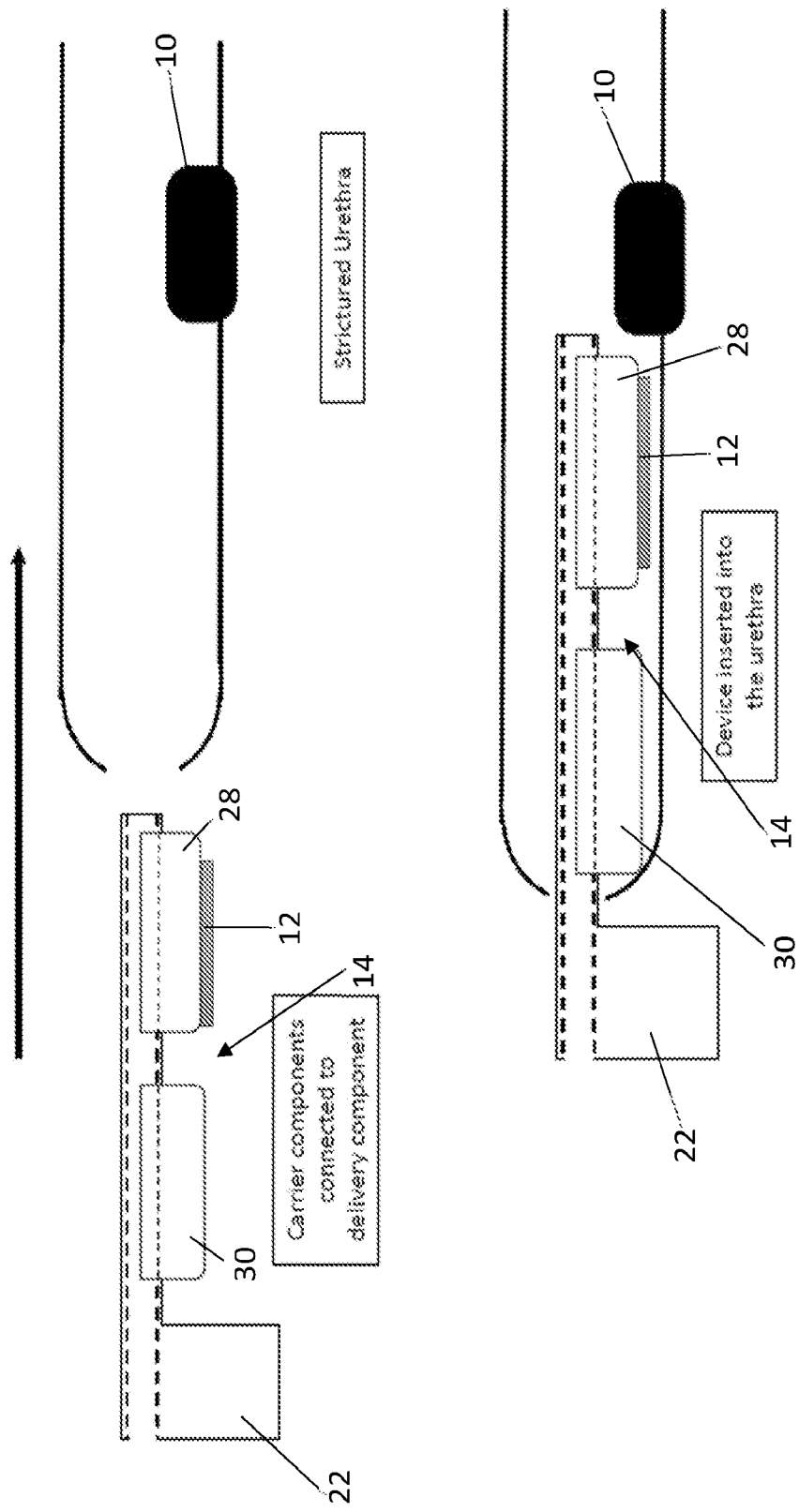

FIG. 3B illustrates a membrane being secured on a carrier component, according to an embodiment of the present invention. As illustrated in FIG. 3B, the carrier component 14 takes the form of one or more attachable and detachable parts 28, 30. In other embodiments, the carrier component 14 may take the form of a solid, non-separable component, as described herein and as would be known to or conceivable to one of skill in the art. Further with respect to FIG. 3B the graft membrane 12 that was harvested for placement at the urethral stricture site 10 is secured to the carrier component 14. The graft membrane 12 can be secured to one single part 28 of the carrier component 14, as illustrated in FIG. 3B, or multiple parts of the carrier component 14, as is known to or conceivable by one of skill in the art. FIG. 3C illustrates the carrier component 14 and the secured graft membrane 12 being coupled to the delivery component 22 for delivery to the urethral stricture site 10. While the parts 28, 30 of the carrier component 14 are shown disposed in a serial fashion on the delivery component in FIG. 3C, the parts 28, 30 of the carrier component 14 can be coupled in parallel, in an offset fashion, or pre-coupled, as is described further herein or would be known to or conceivable by one of skill in the art. FIG. 3D illustrates the carrier component 14 coupled to the delivery component, being inserted into the urethra and advanced to the urethral stricture site 10.

Figure 3E:
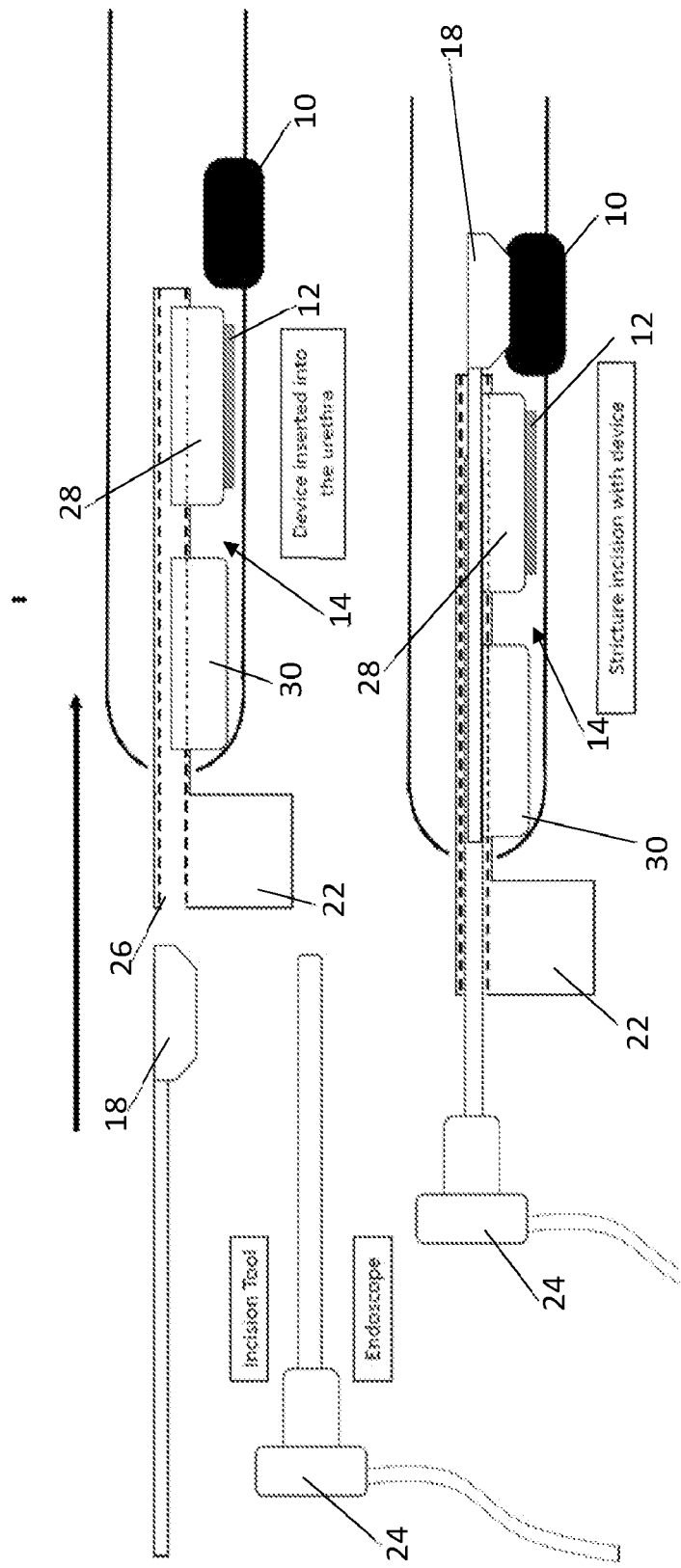
Figure 3F:
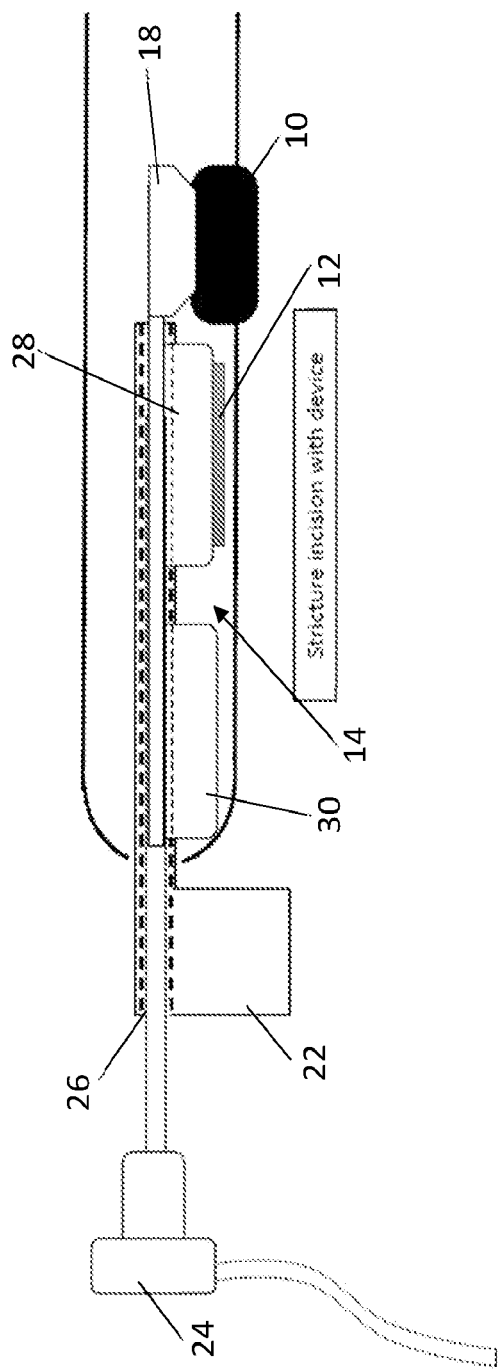

FIG. 3E illustrates an incision tool being inserted through a lumen of the delivery tool into the strictured urethra. The incision tool 18 is used to incise the stricture to prepare the stricture site 10 for placement of the graft membrane 12, also illustrated in FIG. 3E. An endoscope 24 is inserted through the lumen of the delivery component 22 to allow for illumination and visualization of the stricture site 10 during incision and also during placement of the membrane graft 12. Further, FIG. 3F illustrates advancement of the carrier component 14 to the incised urethral stricture site 16 and deployment of the carrier component 14 with the graft membrane at the incised stricture site 16. The placement of the carrier component 14 is visualized using the endoscope 24. As illustrated in FIG. 3F, the carrier component 14 is fixed in place via the expansion of the size of the carrier component 14. However, it should be noted that fixation can be achieved in a number of ways that will be described further herein. The methods of fixation included herein are merely examples and any other suitable form of fixation, known to or conceivable to one of skill in the art could also be used.

Figure 3G:
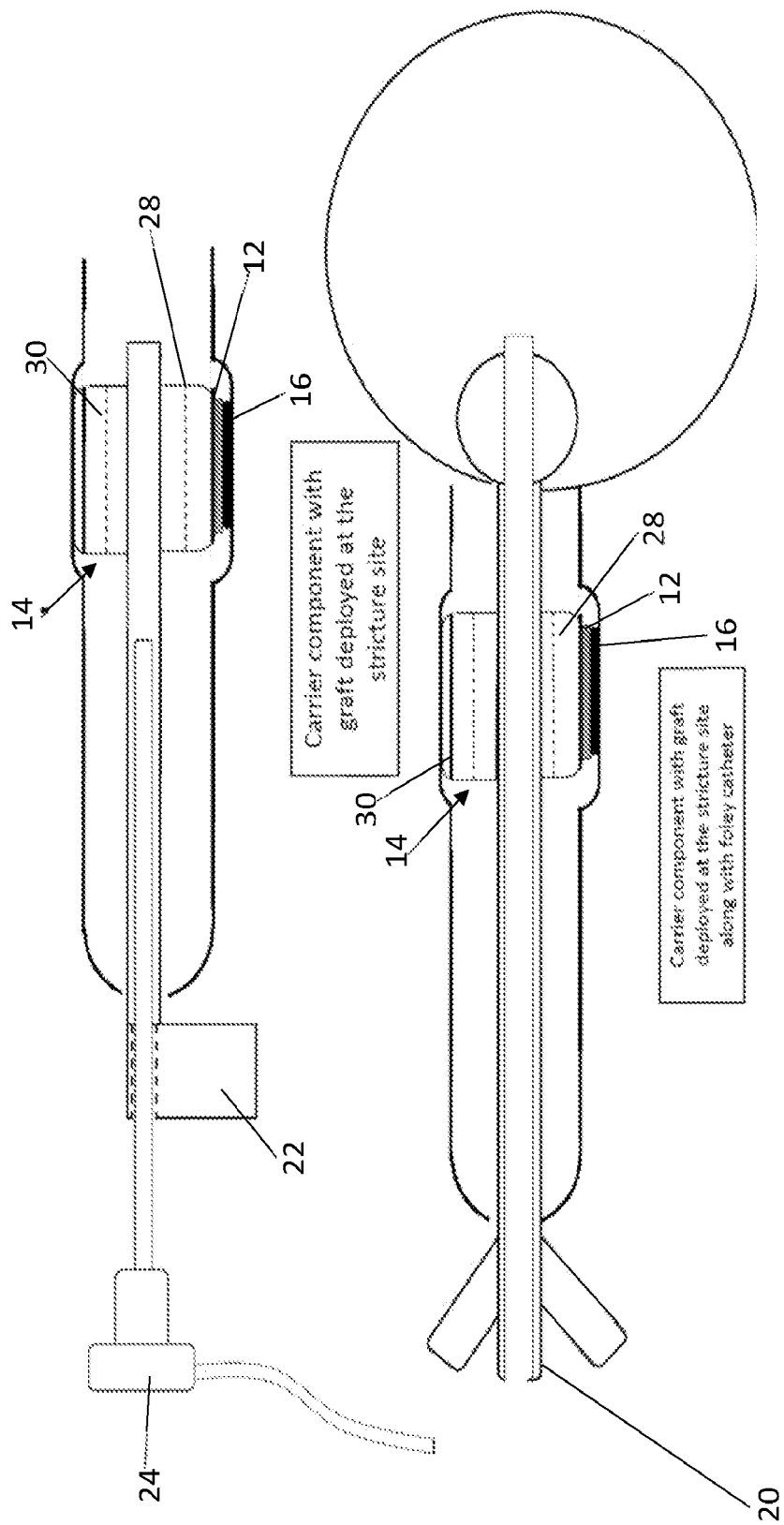
Figure 3H:
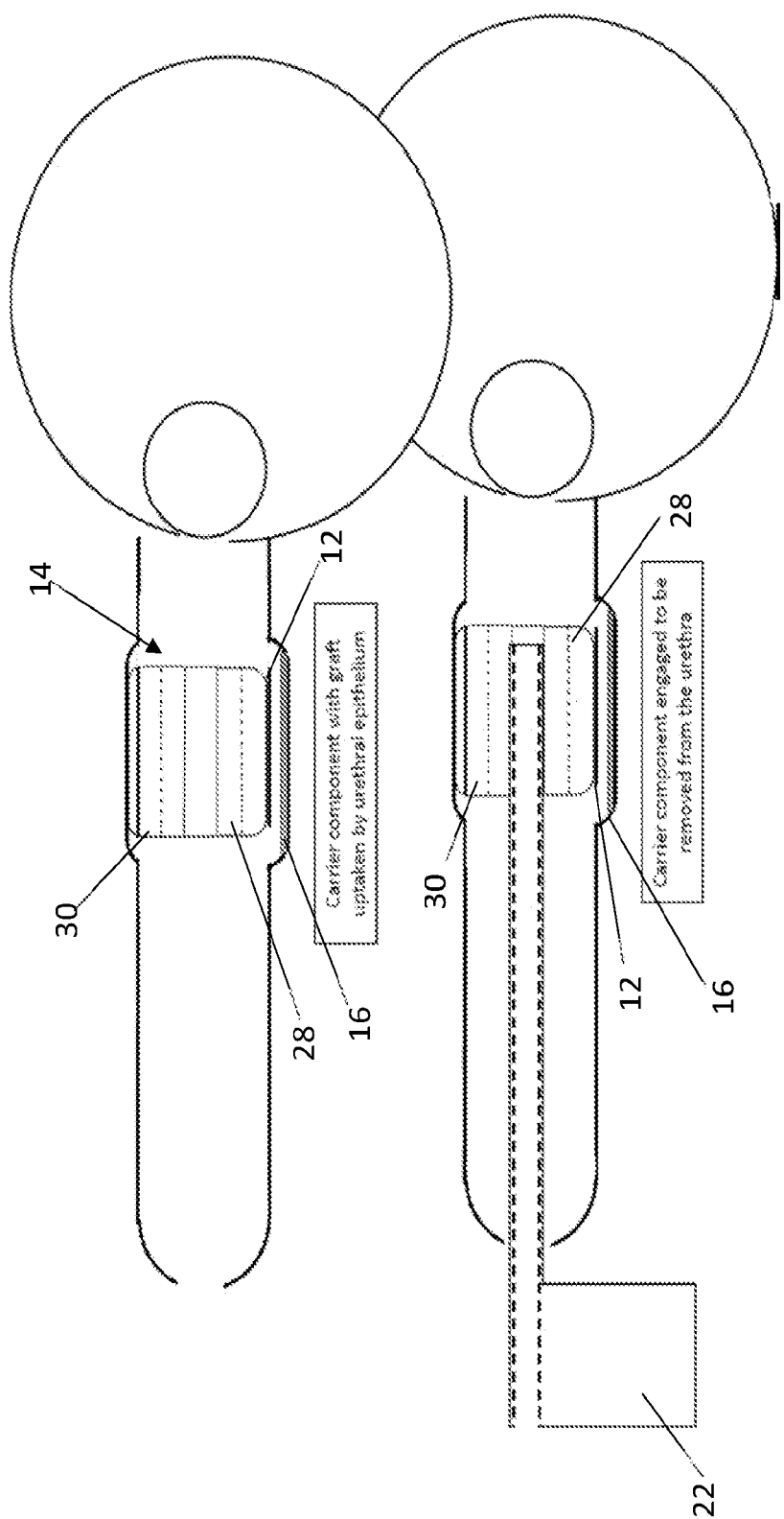
Figure 3I:
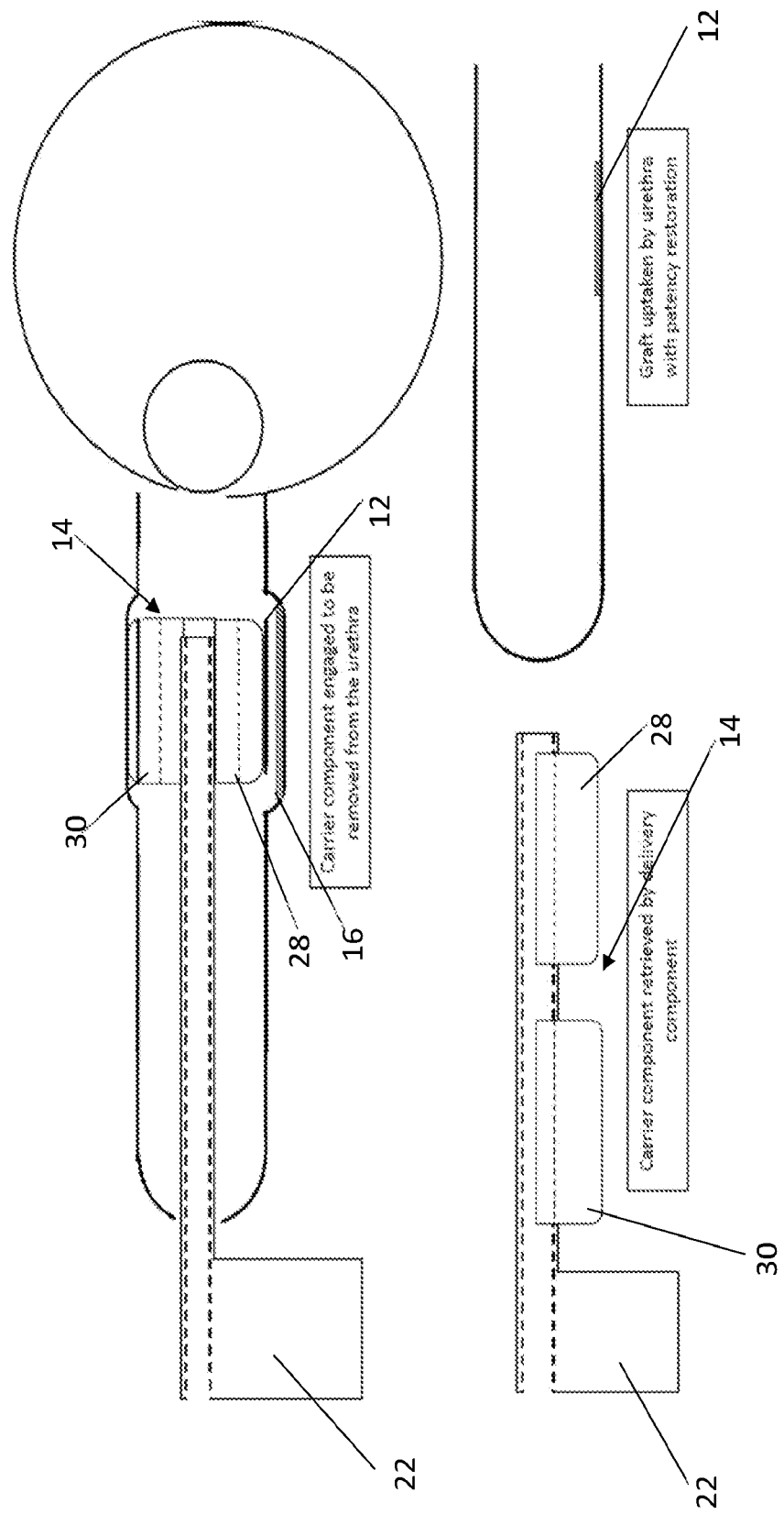

As illustrated in FIG. 3G, the carrier component 14 with the graft membrane 12 is deployed at the incised stricture site 16 and a Foley catheter 20 can then be inserted to allow for the passage of urine during graft adherence. FIG. 3H illustrates the adherence process which can take approximately 7 to 14 days ending with graft adherence to the urethral epithelium. FIG. 3I illustrates the carrier component 14 with the graft adherence to the epithelium complete followed by the carrier component being retrieved by the delivery component. It should be noted that the removal of the carrier component 14 can be completed with the delivery component 22 that advanced the carrier component to the urethral stricture site or with a separate removal component configured for the removal of the carrier component. The graft membrane 12 is left behind with urethral patency restored.

Figure 4:
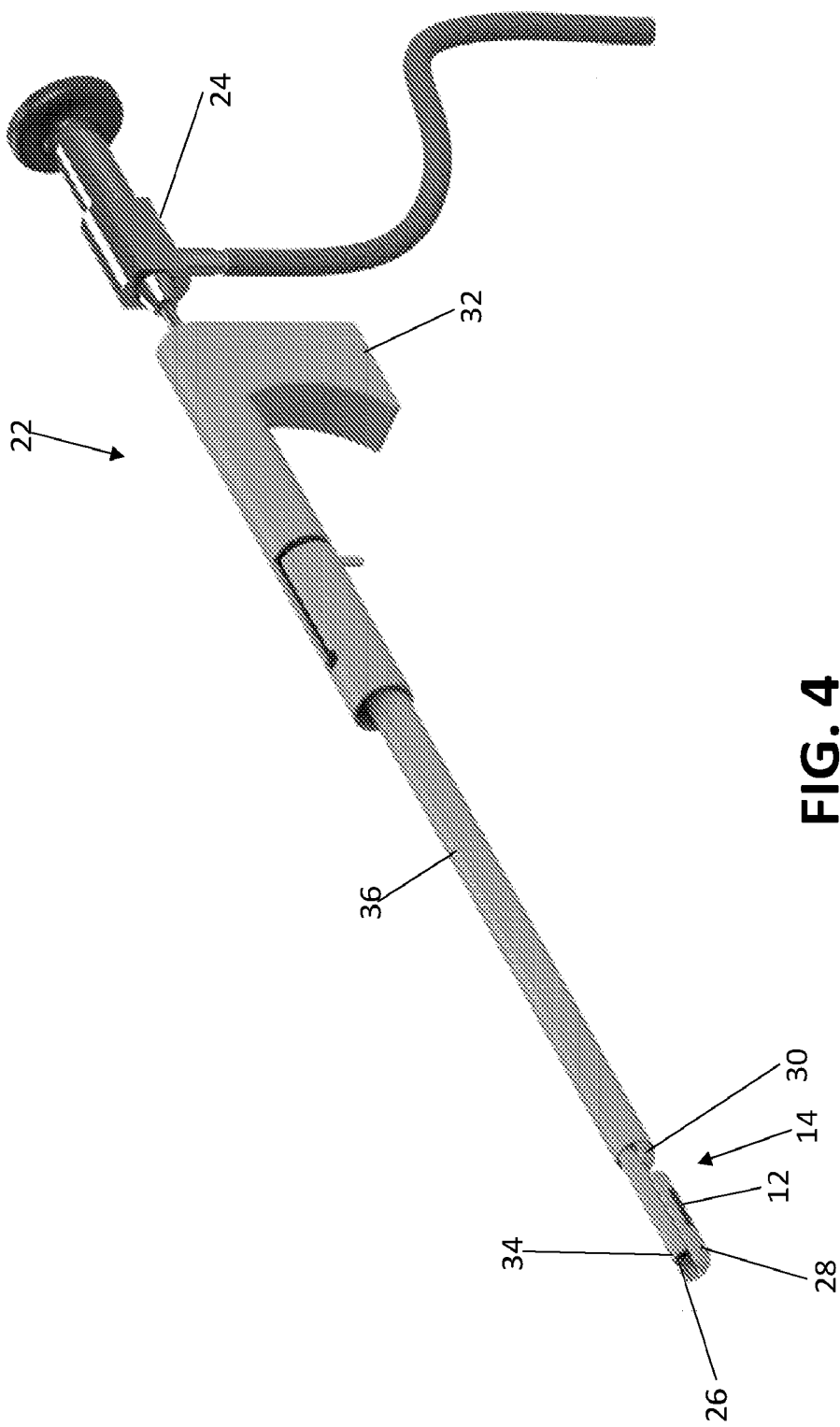
FIG. 4 illustrates a perspective view of a delivery component and a graft carrier component, according to an embodiment of the present invention.

FIG. 4 illustrates a perspective view of a delivery component and a graft carrier component, according to an embodiment of the present invention. The delivery component 22 includes a proximal end 32 and a distal end 34. The proximal end 32 is configured for control of the delivery component 22, while the distal end 34 is configured to deliver a graft carrier component 14 to the incised stricture site 16, not pictured. The delivery component 22 also includes an elongated generally cylindrical member 36 that defines a lumen 26. The elongated generally cylindrical member 36 is configured to be advanced through the urethra of the subject and is generally 36 French or smaller. The lumen 26 is configured to receive tools including a blade for incising the stricture, illumination device, scopes, fiber optics, laser fibers, ultrasound, or other tools known to or conceivable to one of skill in the art. It is also possible that the lumen 26 may include a single passage or multiple passages for use of multiple tools simultaneously.

A delivery component 22 according to the present invention can include a mechanism for positioning or targeting of the urethral stricture site. These mechanisms can include visualization, markers, marks of measure, or other targeting mechanisms known to or conceivable by one of skill in the art. These mechanisms can also be used for measurement of length or distances within the urethra during the procedure. The delivery component 22 of the present invention can accommodate the use of a blade for incision of the stricture site. In some embodiments, the device for treatment of urethral strictures can include a blade for this purpose. The device can also include a mechanism for urine diversion.

Figure 5A:
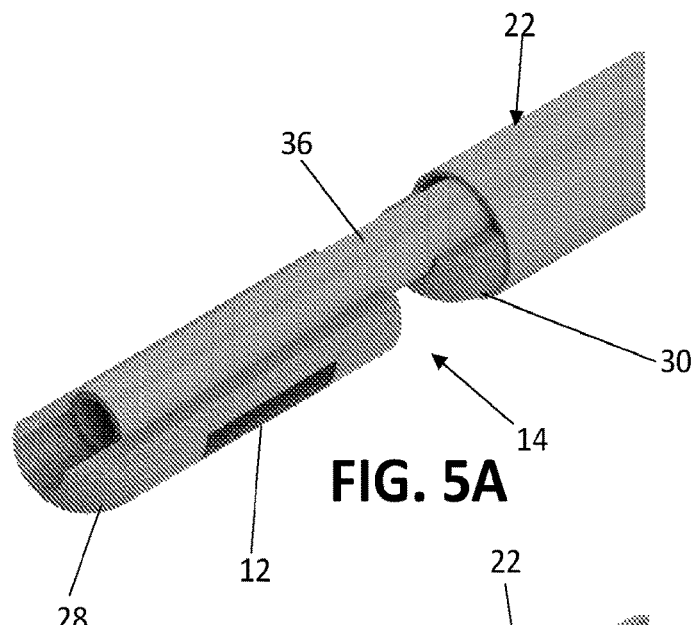
FIGS. 5A-5C illustrate perspective views of a distal end of the delivery component and the graft carrier component, according to an embodiment of the present invention.
Figure 5B:
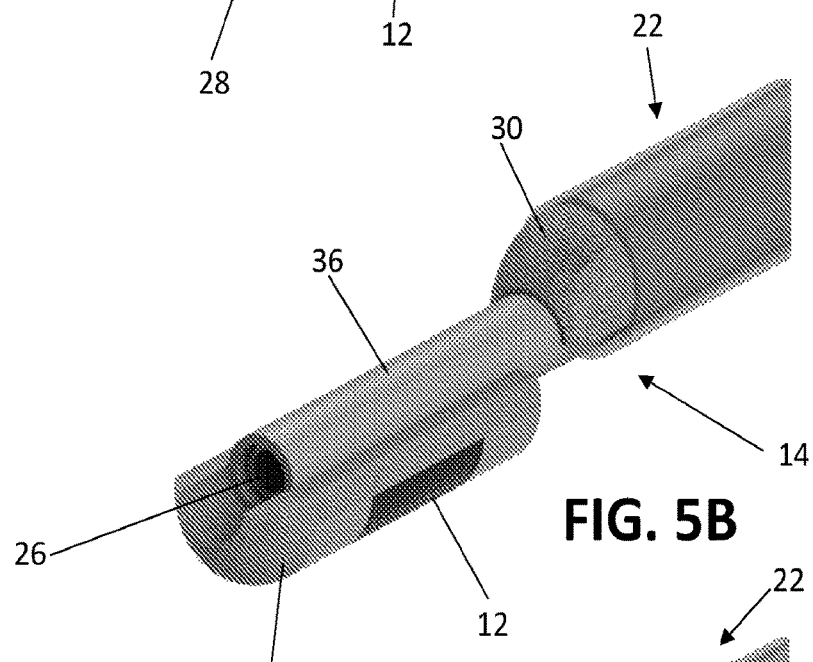
Figure 5C:
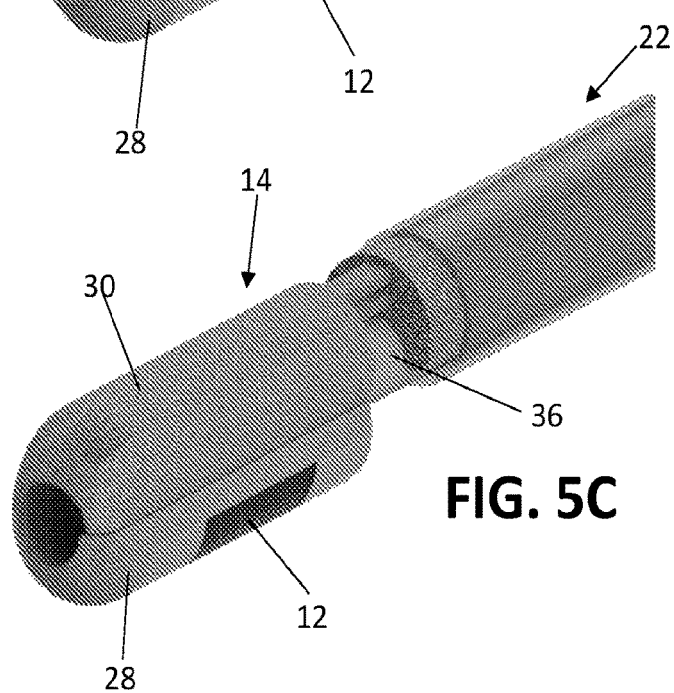

FIGS. 5A-5C illustrate perspective views of a distal end of the delivery component and the graft carrier component, according to an embodiment of the present invention. FIGS. 5A-5C illustrate one possible embodiment for the graft carrier component 14. In this embodiment of the graft carrier component 14, the graft carrier component 14 is delivered in two separate parts 28, 30. The two parts 28, 30 of the graft carrier component 14 are disposed in serial, in this embodiment. The part 28 that carries the graft 12 is disposed distal to the second part 30. The two parts 28, 30 and can be configured to lock together with a locking mechanism. The locking mechanism can be any locking mechanism known to or conceivable to one of skill in the art, such as frictional locking or male and female locking components. During a procedure, the first part 28 is aligned with the incised urethral stricture site 16, not pictured. Then, the distal second part 30 is rotated using the control mechanisms of the delivery device 22, such that the second piece 30 is disposed just proximal to the first piece 28, and in such a way, that if the second piece 30 is advanced distally, the generally cylindrical shape is completed, as illustrated in FIG. 5B. The second part 30 is then advanced and locked together with the first part 28, as illustrated in FIG. 5C. The advancement results in a larger lumen expansion when the two parts 28, 30 are alongside each other, than when they entered the lumen serially. Once the two parts 28, 30, are locked together, in some embodiments the graft carrier component 14 can be expanded to create a wide enough lumen at the stricture site 10. In another embodiment, the two parts 28, 30 are disposed serially and rotationally offset, so as to enter the urethra in an s-shape, and the distal second part 30 is advanced to align with the first part 28 completing a generally cylindrical shape. In other embodiments, the carrier component 14 may consist of more than two parts, and parts may be connected. In some embodiments, an inner sheath may be a third carrier component part. In other embodiments fixation may be achieved through a fixation component such as pins, barbs, sutures, or other fixation methods known to or conceivable to one of skill in the art.

Figure 6:
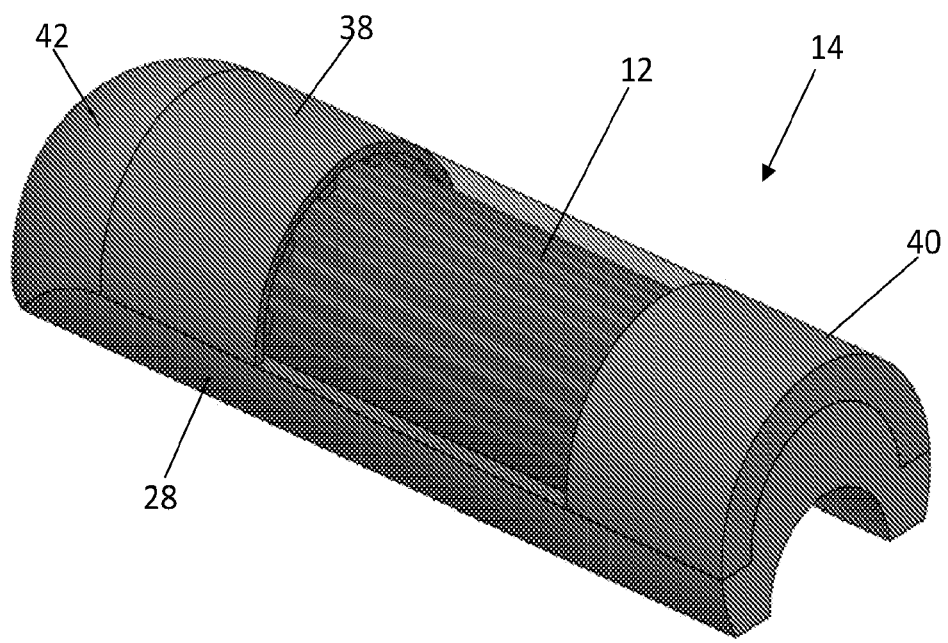
FIG. 6 illustrates a perspective view of a graft holding piece of the graft carrier component, according to an embodiment of the present invention.

FIG. 6 illustrates a perspective view of a graft securement part of the graft carrier component, according to an embodiment of the present invention. As illustrated in FIG. 6, the graft membrane 12 can be secured to the part 28 of the graft carrier component 14 by platens 38, 40. These platens 38, 40 sit atop edge portions of the graft membrane 12, to hold the graft membrane 12 in place during delivery and adherence. These platens 38, 40 cause necrosis of the graft tissue beneath them, to eliminate tearing during removal of the graft carrier component 14, after adherence. The graft membrane can be perforated or not perforated, according to physician preference and patient need, before it is mounted on the graft carrier component 14. The graft carrier component 14 can also include an end cap 42, to facilitate insertion of the device through the urethra.

Figure 7A:
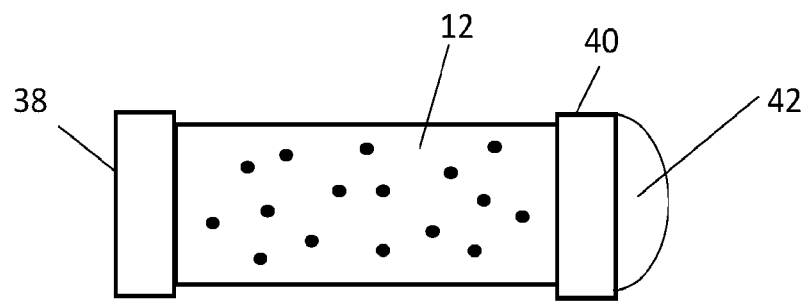
FIGS. 7A and 7B illustrate top down views of graft carrier components, according to an embodiment of the present invention.
Figure 7B:
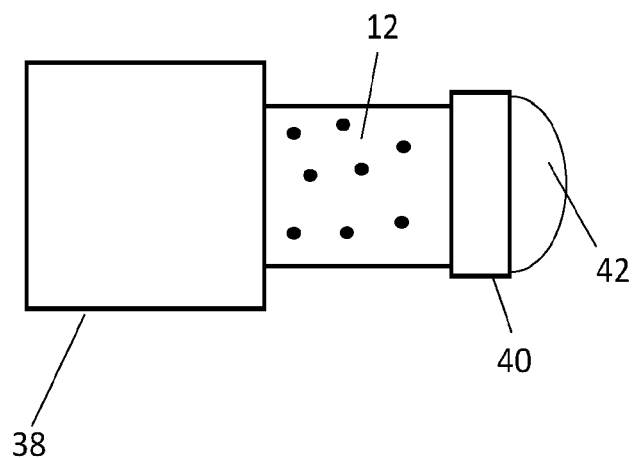

FIGS. 7A and 7B illustrate top down views of graft carrier components, according to an embodiment of the present invention. As described with respect to FIG. 6, the graft membrane 12 is secured by platens 38, 40. As illustrated in FIGS. 7A and 7B the size of these platens 38, 40 can vary based on physician preference, patient need, and desired graft size. FIG. 7A illustrates a small set of platens 38, 40 to allow for a large graft adherence region. FIG. 7B illustrates varied size platens 38, 40 to limit graft adherence size. The size of the platens 38, 40 can take any size or combination of sizes known to or conceivable to one of skill in the art. End cap 42 is disposed distal to the distalmost platen 40.

Figure 8A:
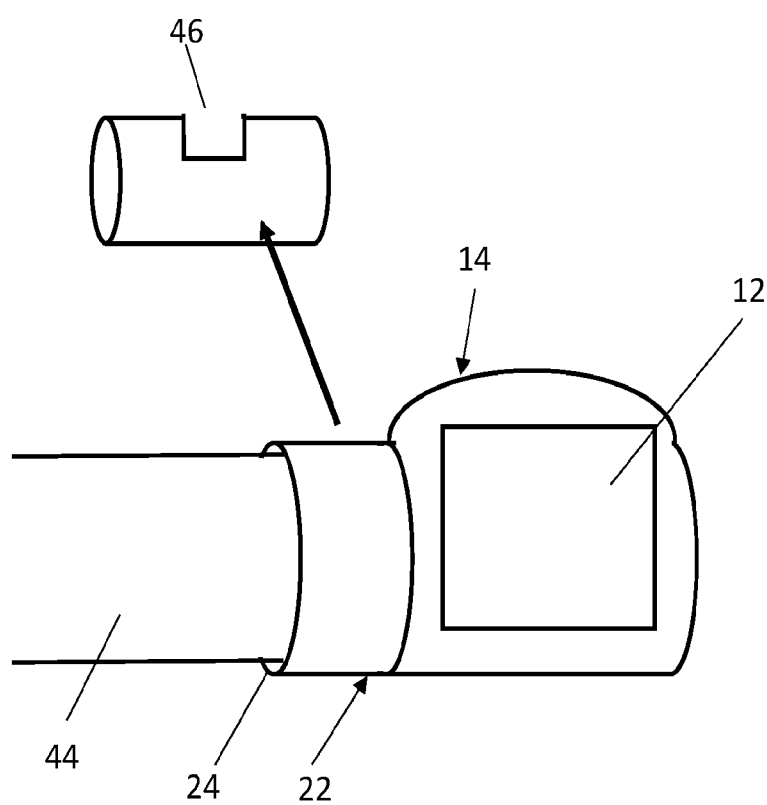
FIG. 8A-8C illustrate side views of an inner sheath, according to an embodiment of the present invention.
Figures 8B, 8C:
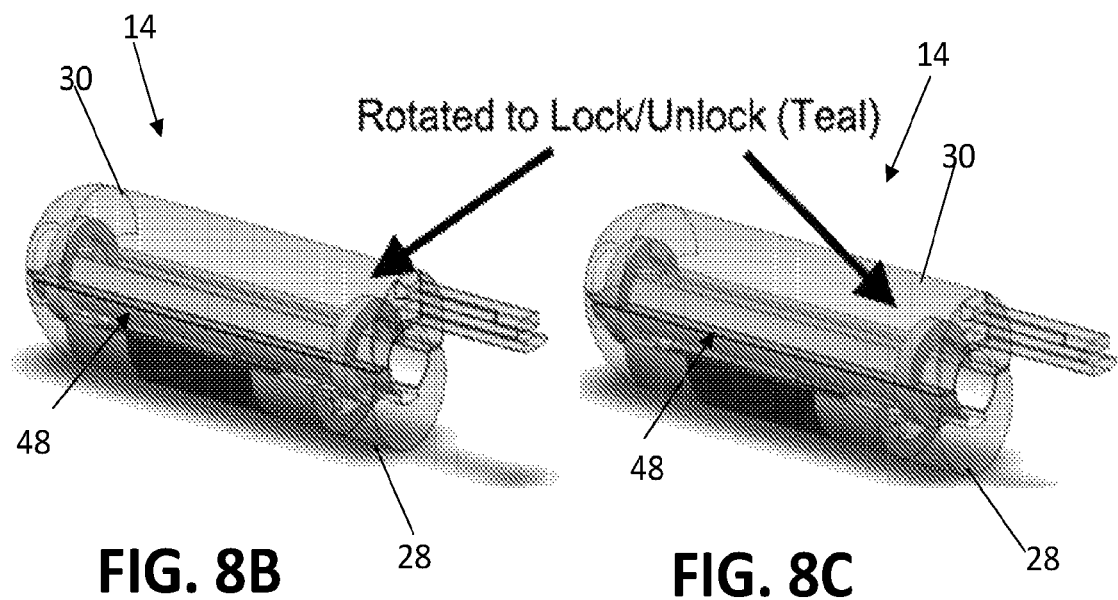

FIG. 8A-8C illustrate side views of an inner sheath, according to an embodiment of the present invention. An inner sheath 44, which can be disposable, is inserted into the lumen 26 of the delivery component 22, before the graft membrane 12 is loaded onto the graft carrier component 14. The distal end 30 of the delivery device 22 includes a slot 46 to guide loading of the inner sheath 44, as illustrated in FIG. 8A. The inner sheath 44 may be disposable and is used for controlling the locking mechanism for the graft carrier component 14 to lock the first and second parts 28, 30 together into the generally cylindrical shape, as illustrated in FIGS. 8B and 8C. The inner sheath 44 is rotated within the graft carrier component 14 to engage the locking mechanism and lock the two carrier component parts 28, 30 together. Some embodiments of the device could also include a removal sheath for removal of the graft carrier component from the urethra. The inner sheath for delivery and the inner sheath for removal would include slightly different geometry to account for the opposite direction of rotation for locking and unlocking the graft carrier component parts. Locking/unlocking mechanisms (subject to wear) are all located on components which can be disposable. This protects the delivery device 22 from wear if it is intended to be sterilized and reused. In some embodiments, the inner sheath 44 allows for 4-point/corner locking of the graft carrier component 44. In some embodiments, the inner sheath 44 is also designed to work with an incising blade to protect the urethral lumen until the blade is deployed. The inner sheath 44 can be formed from a material that provides the inner sheath 44 with friction free properties, such a material can take the form of a lubricious material.

Figures 9A, 9B:
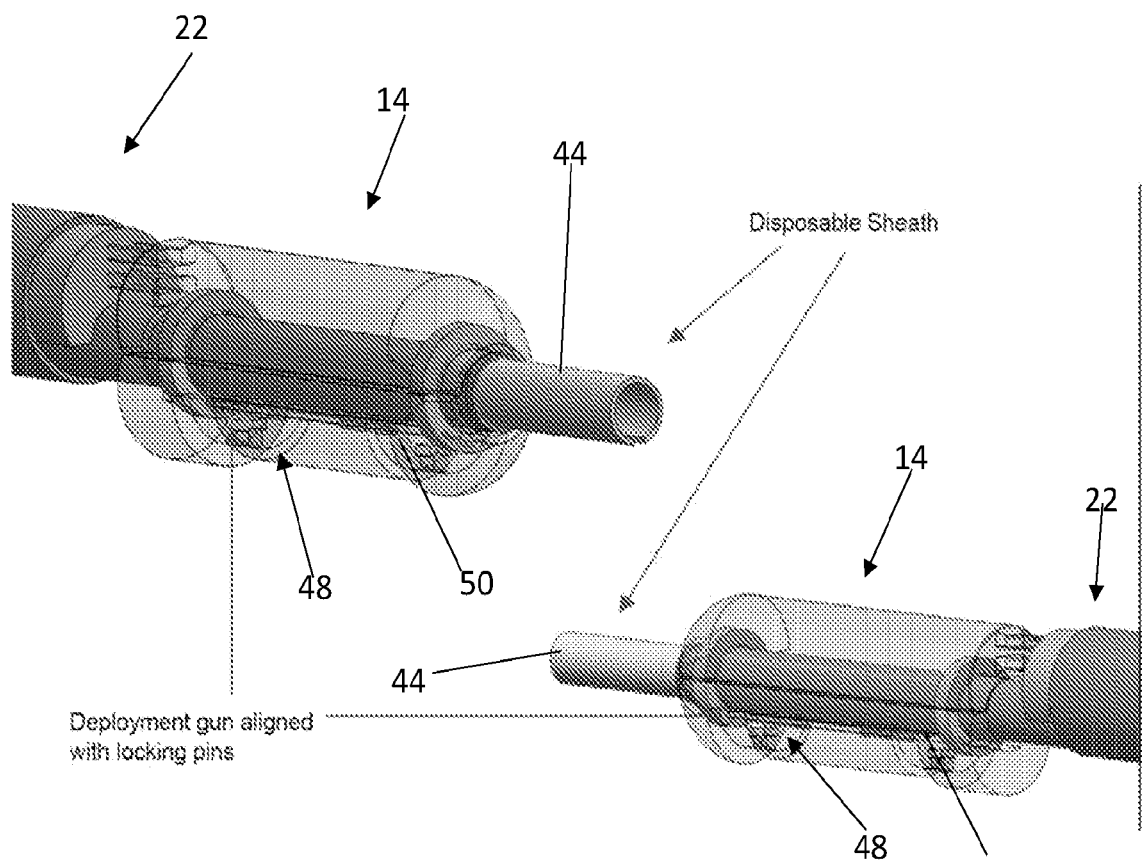
FIGS. 9A and 9B illustrate a locking mechanism of the graft carrier component being engaged with an inner sheath, while the graft carrier component is disposed on the deployment component, according to an embodiment of the present invention.
Figures 14A, 14B, 14C:
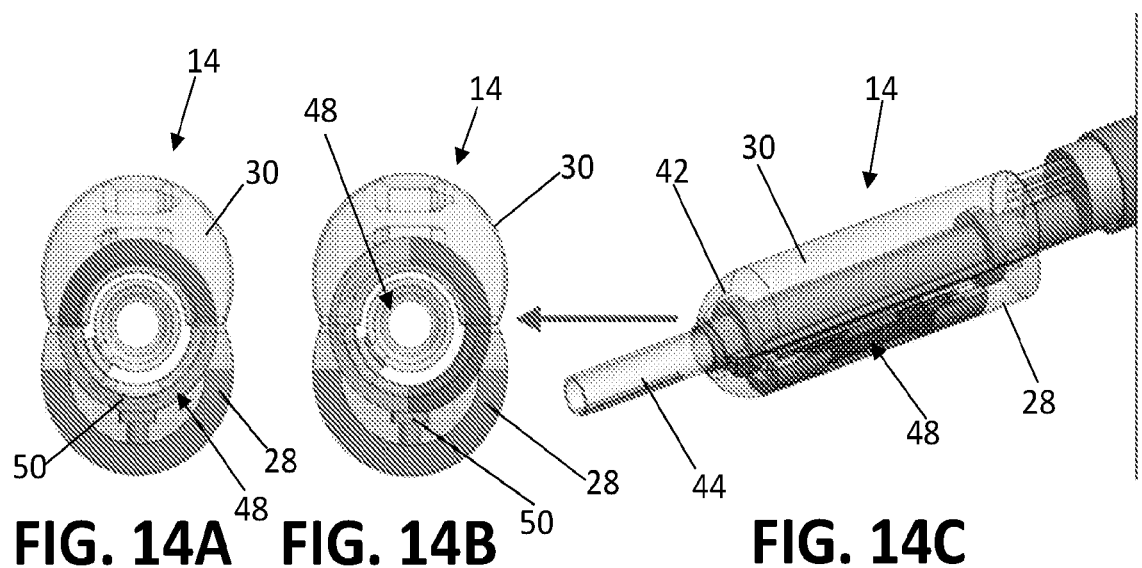
FIGS. 14A-14C illustrate sectional and perspective views of the actuation of the locking mechanism, according to an embodiment of the present invention.

FIGS. 9A and 9B illustrate a locking mechanism of the graft carrier component being engaged with an inner sheath, while the graft carrier component is disposed on the deployment component, according to an embodiment of the present invention. The inner sheath 44 engages the locking mechanism 48, and the deployment component is aligned with locking pins 50 within the locking mechanism 48. FIGS. 14A-14C illustrate sectional and perspective views of the actuation of the locking mechanism 48, according to an embodiment of the present invention.

Figure 10:
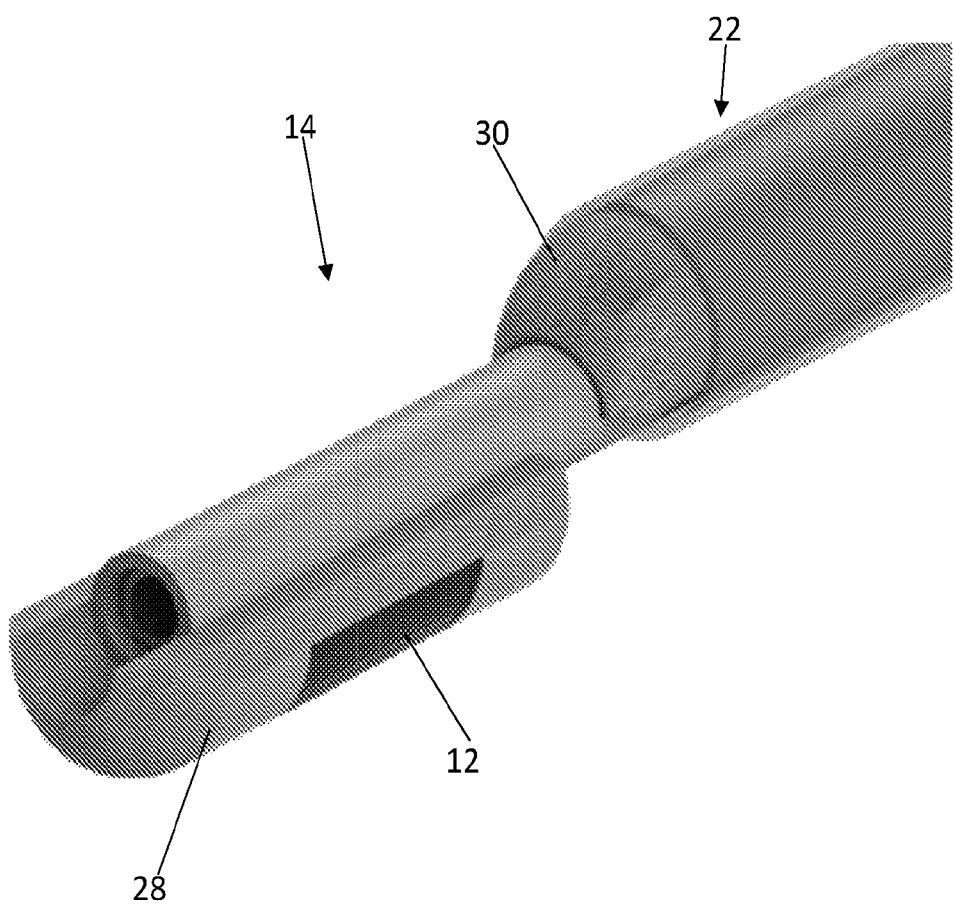
FIGS. 10 and 11 illustrate another embodiment of a graft carrier component and delivery component, according to an embodiment of the present invention.
Figure 11:
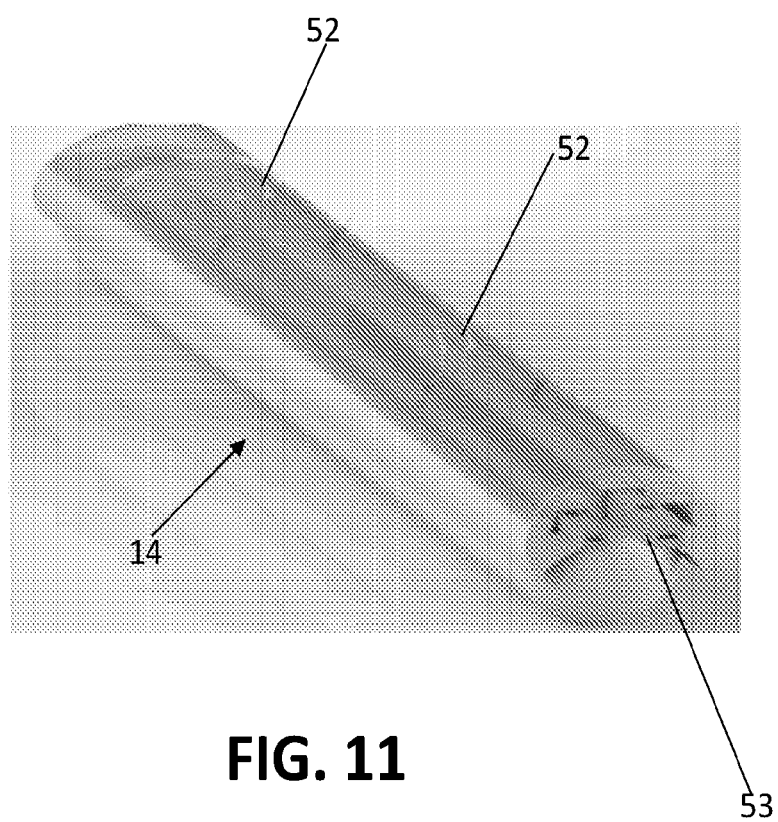
Figure 13A:
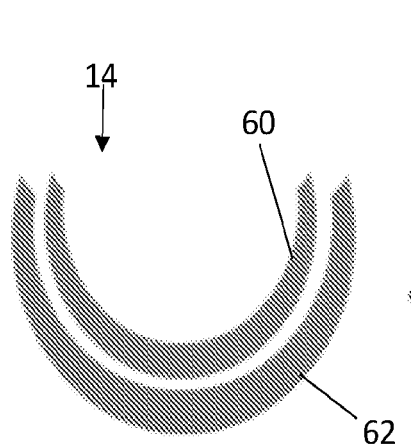
FIGS. 13A-13D illustrate another embodiment for a graft carrier component, according to an embodiment of the present invention.
Figure 13B:
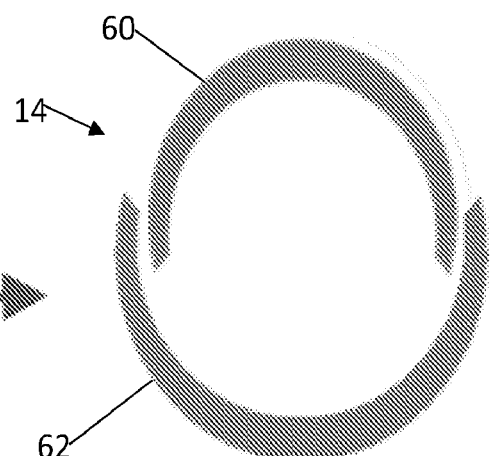
Figure 13C:
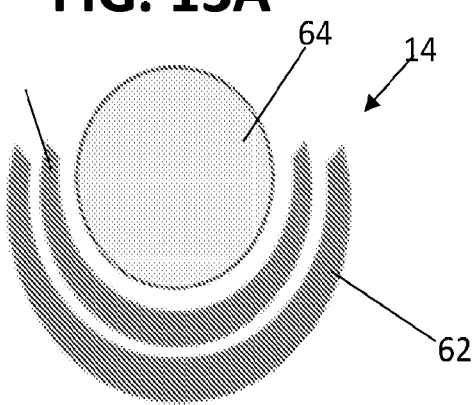
Figure 13D:
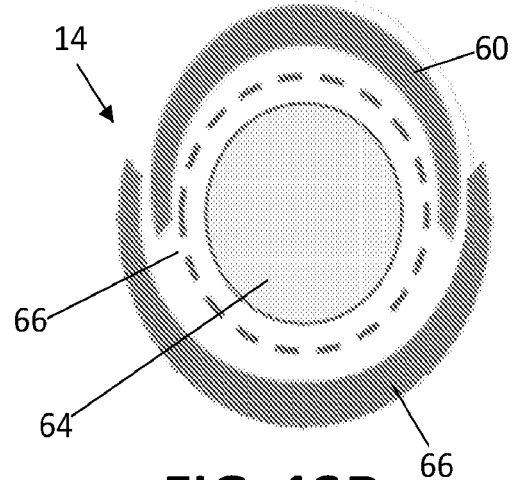

In some embodiments, the locking mechanism 48 may be contained in the lumen of the carrier component 14, and engaged rotationally by the inner sheath 44. In some embodiments, the locking mechanism 48 may be engaged on the ends of the carrier component with rotational engagement, or longitudinal engagement. In some embodiments the locking mechanism 48 may take place alongside the outer edges of the carrier component 14 parts 28, 30. In some embodiments, the locking mechanism 48 may coincide with mechanisms for separating the carrier component 14 from the delivery component 22. In some embodiments, the carrier component loading mechanism will integrate with the inner sheath 44. In some embodiments the carrier component loading mechanisms will be integrated with the delivery component 22. FIGS. 10 and 11 illustrate another embodiment of a graft carrier component and delivery component, according to an embodiment of the present invention. As illustrated in FIG. 10, the parts 28, 30 of the graft carrier component 14 can be delivered in an offset state. A short distance can be left between the first piece 28 and the second piece 30 during delivery to prevent too large a profile on entry. This design streamlines the delivery process, as the second piece 30 does not need to be rotated into place for advancement and locking. The second piece 30 only needs to be advanced and locked with the first piece 28. As illustrated in FIG. 11, the graft carrier component 14 of the embodiment of FIG. 10, or any other embodiment known to or conceivable by one of skill in the art can include urethral fixation pins 52 for holding the graft carrier component 14 in place in the urethra during adherence. As illustrated in FIG. 11, the urethral fixation pins 52 work by moving rods 54 inside the implant forward or backward. The rods 53 are actuated by the user at the proximal end 32 of the delivery component 22 of the device. The urethral fixation pins 52 can be angled, opposing longitudinal pins that extend from slanted holes defined by the graft carrier component 14. In some embodiments, the graft carrier component 14 includes 4 urethral fixation pins 52 with a depth of approximately 2-4 mm. The pins 52 can extend at radial opposing angles to avoid rotation. Any other suitable fixation mechanism known to or conceivable to one of skill in the art can also be used. FIGS. 12A-12C illustrate another embodiment for a graft carrier component, according to an embodiment of the present invention. As illustrated in FIGS. 12A-12C, two comb-like interleaved arcs 54, 56 are connected by a flexible joint 58 or a hinge to form the graft carrier component 14. The profile of the graft carrier component 14 when the inter-leaved arcs are collapsed is small enough to travel through the urethra. The graft membrane 12, not pictured, is placed along the external, exposed side of the graft carrier component 14 in this configuration. The graft carrier component 14 is actuated at the joint or hinge 58 to open the combs 54, 56 to an expanded state. Possible sources of the actuation include a motor, spring, pull wire, shape memory metal, or any other source of actuation known to or conceivable to one of skill in the art. FIGS. 13A-13D illustrate another embodiment for a graft carrier component, according to an embodiment of the present invention. As illustrated in FIGS. 13A-13D, the graft carrier component 14 includes concentric or inscribed generally half-circular shapes 60, 62 that are deployed into a generally cylindrical shape for graft adherence. The inner generally half-circular shape 60 is rotated approximately 120-180 degrees to form a larger, generally cylindrical shape with the outer generally half-circular shape 62. The generally half-circular shapes 60, 62 are inscribed, rather than serial, and have a constrained inner lumen size 64 during delivery. Upon delivery and rotation into the generally cylindrical shape, the constrained inner lumen 64 is expanded into an expanded inner lumen 66.

Figure 15:
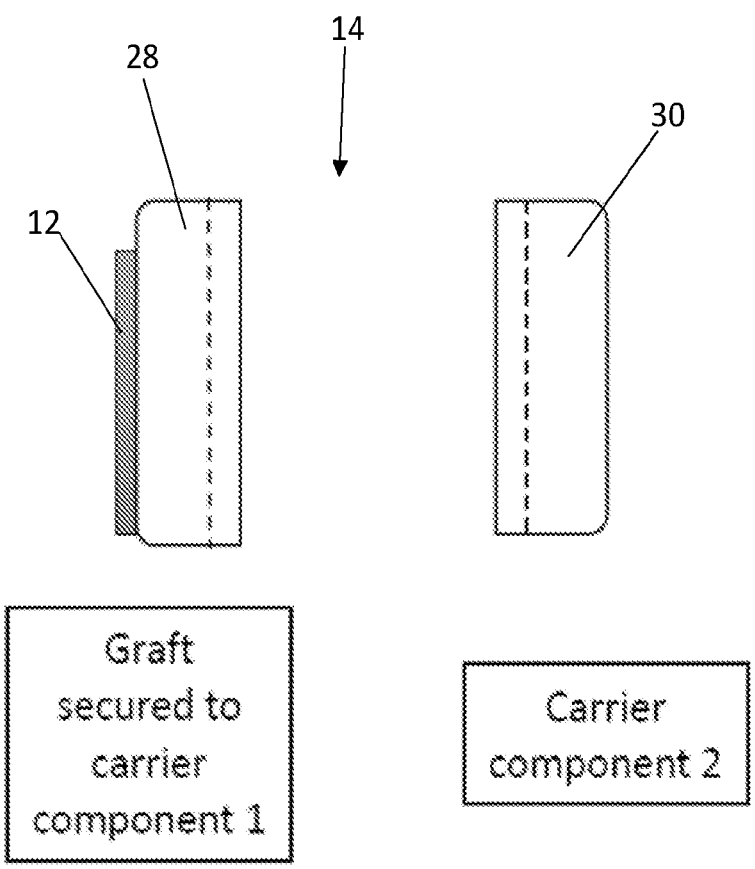
FIGS. 15-17 illustrate side views of carrier components, according to embodiments of the present invention.
Figure 16:
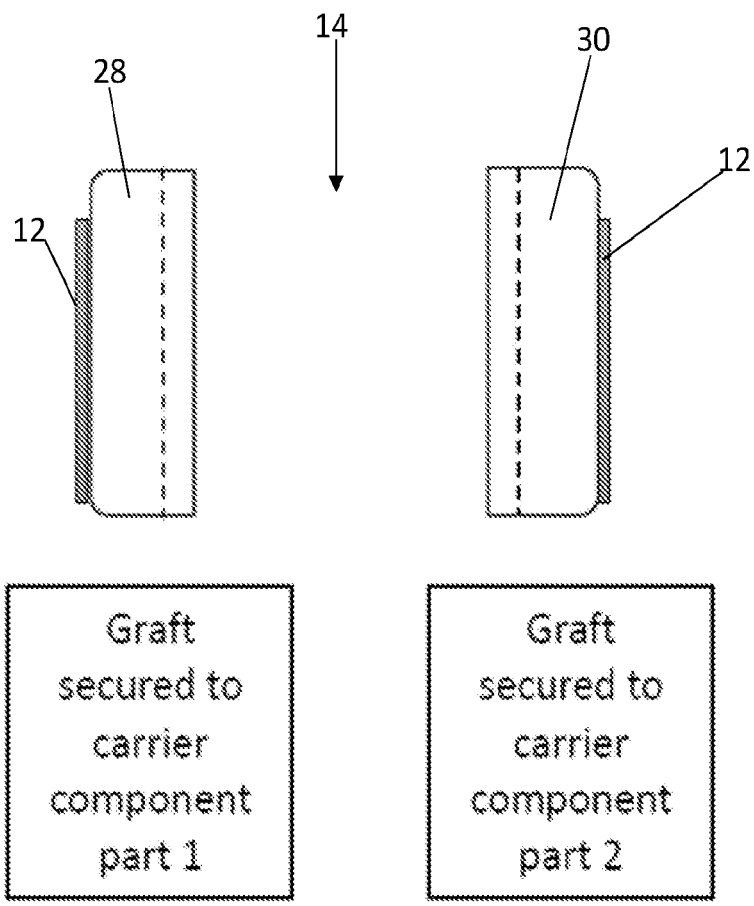
Figure 17:
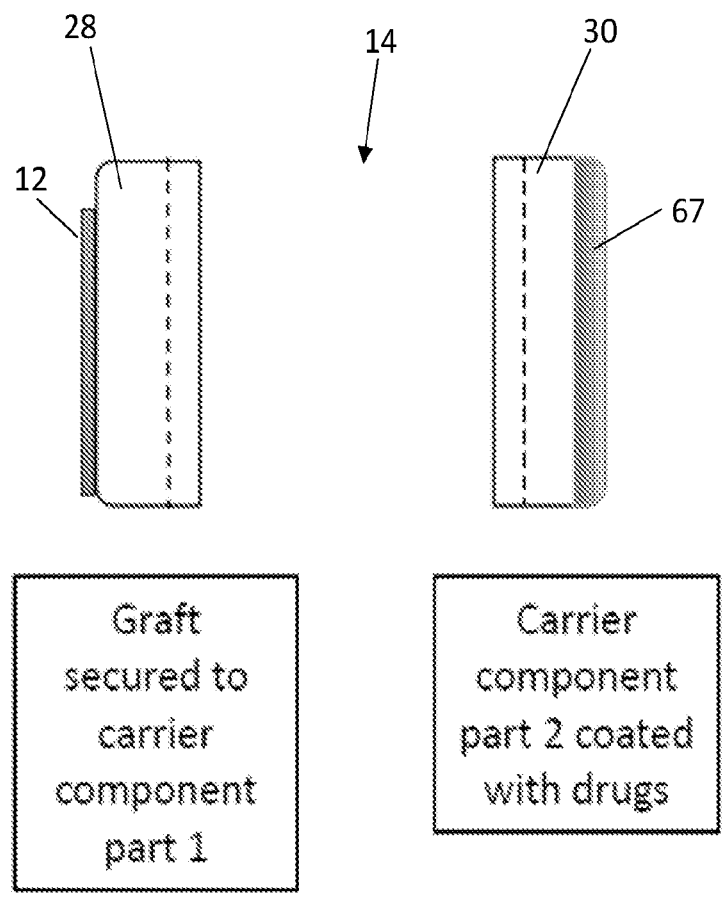

FIGS. 15-17 illustrate side views of carrier components, according to embodiments of the present invention. FIG. 15 illustrates the graft membrane 12 being secured onto one carrier component part 28, wherein the carrier component 14 takes the form of two or more parts that are attachable and detachable. FIG. 16 illustrates another embodiment where the graft membrane 12 is secured to more than one carrier component part 28, 30, wherein the carrier component 14 takes the form of two or more parts that are attachable and detachable. The graft membrane 12 can take the form of one single piece of graft membrane or multiple pieces of graft membrane. FIG. 17 illustrates another embodiment where the graft membrane 12 is secured on one part 28 of the carrier component 14 and a drug or growth factor 67 is applied to either part 28, 30 of the carrier component 14, wherein the carrier component 14 takes the form of two or more parts that are attachable and detachable.

Figure 18:
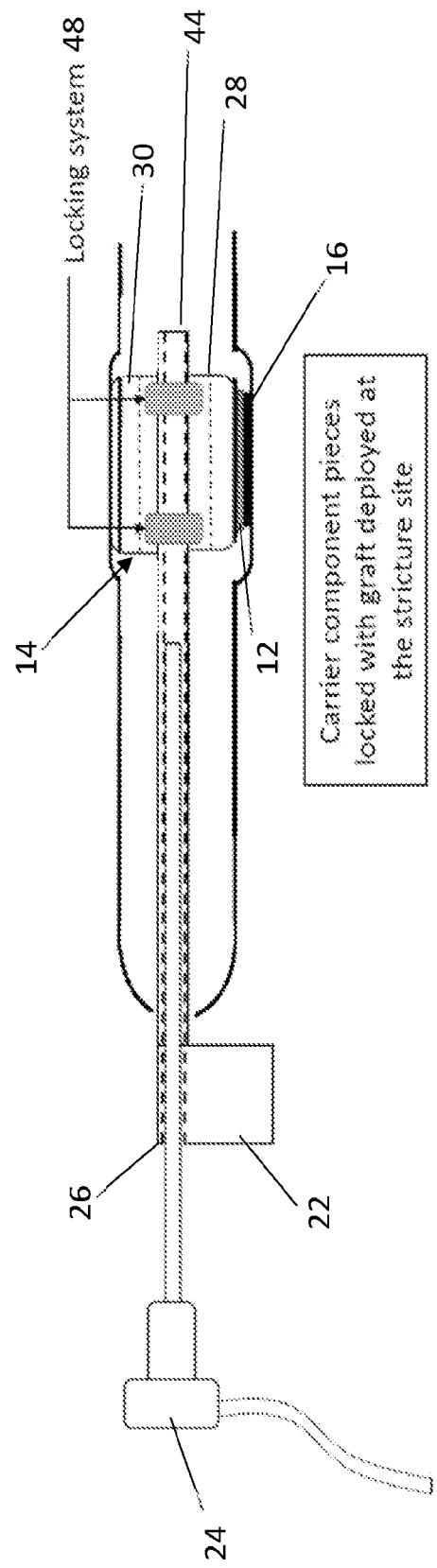
FIGS. 18 and 19 illustrate side views of locking mechanisms for the carrier component, according to embodiments of the present invention.
Figure 19:
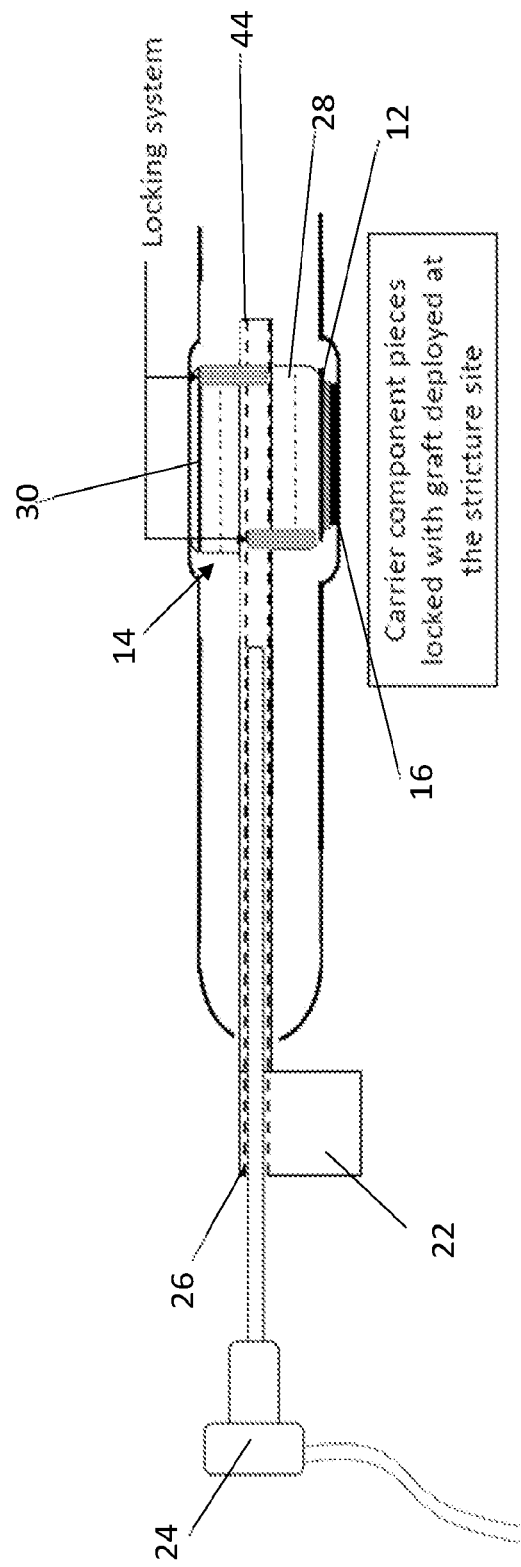

FIGS. 18 and 19 illustrate side views of locking mechanisms for the carrier component, according to embodiments of the present invention. FIG. 18 illustrates parts 28, 30 of the carrier component 14 locking to one another after they are positioned at or near the stricture site 10 or incised stricture site 16, either before or after graft deployment. While an internal locking mechanism 48 is shown in FIG. 18, the locking mechanism can be either external or internal to the carrier component parts 28, 30. FIG. 19 also illustrates carrier component parts 28, 30 locking to one another after they are positioned at or near the stricture site 10 or incised stricture site 16, either before or after graft deployment. While an external locking mechanism 48 is shown in FIG. 19, the locking mechanism can be either external or internal to the carrier component parts 28, 30. The locking mechanism can be engaged either rotationally or longitudinally, or in any other way known to or conceivable by one of skill in the art.

Figure 20:
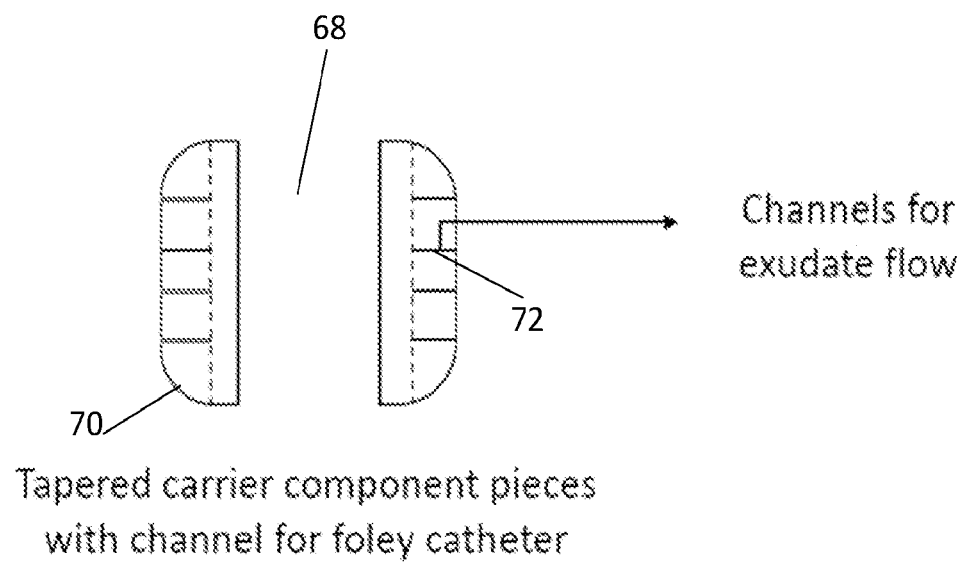
FIG. 20 illustrates a side view of an embodiment of a carrier component according to an embodiment of the present invention.

FIG. 20 illustrates a side view of an embodiment of a carrier component according to an embodiment of the present invention. As illustrated in FIG. 20, the carrier component 14 can define an inner channel through which a Foley catheter 20, not pictured, can be disposed. The carrier component 14 can have end surfaces 70 that are tapered. Further the carrier component surfaces may have microslots/pores 72 for exudate flow. The carrier component 14 can also have surface finishing that is optimized to increase the friction between the urethral epithelium and prevent migration. The carrier component 14 can take the form of a single part or multiple parts as described herein.

Figure 21:
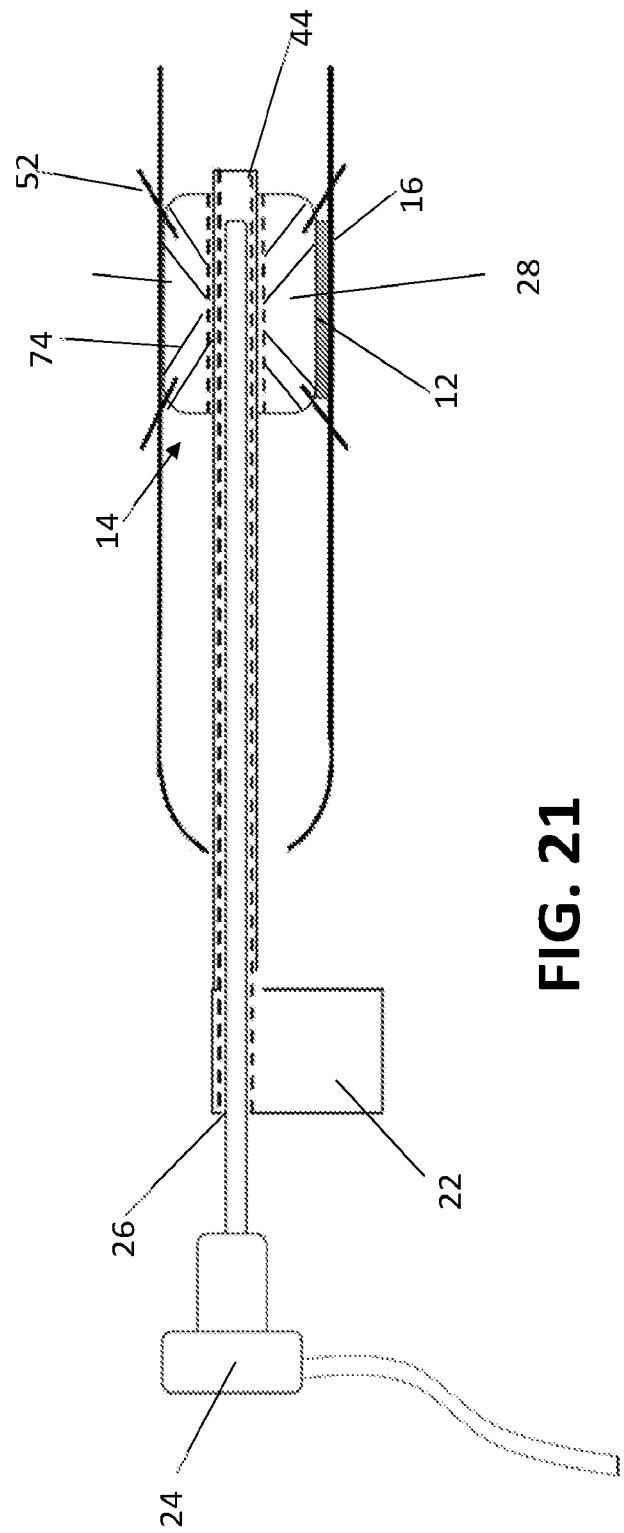
FIG. 21 illustrates a side view of carrier component fixation at the stricture site, according to an embodiment of the present invention.

FIG. 21 illustrates a side view of carrier component fixation at the stricture site, according to an embodiment of the present invention. The carrier component 14 may define passages 74 for fixation elements 52 such as pins, as illustrated in FIG. 21. Alternately, the fixation elements 52 could include tacks, and/or sutures. The pins, tacks, and/or sutures are included as examples of carrier component fixation and any other suitable solution for carrier component fixation known to or conceivable by one of skill in the art could also be used.

Figure 22:
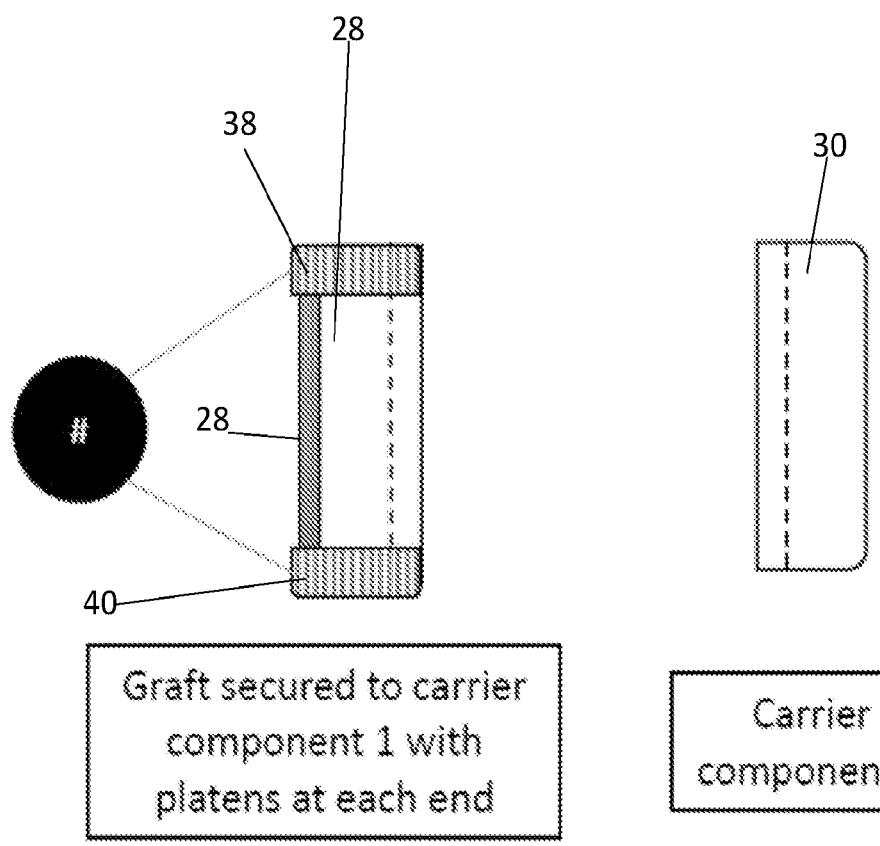
FIGS. 22 and 23A-23D illustrate side views of graft securement components, according to embodiments of the present invention.
Figure 23:
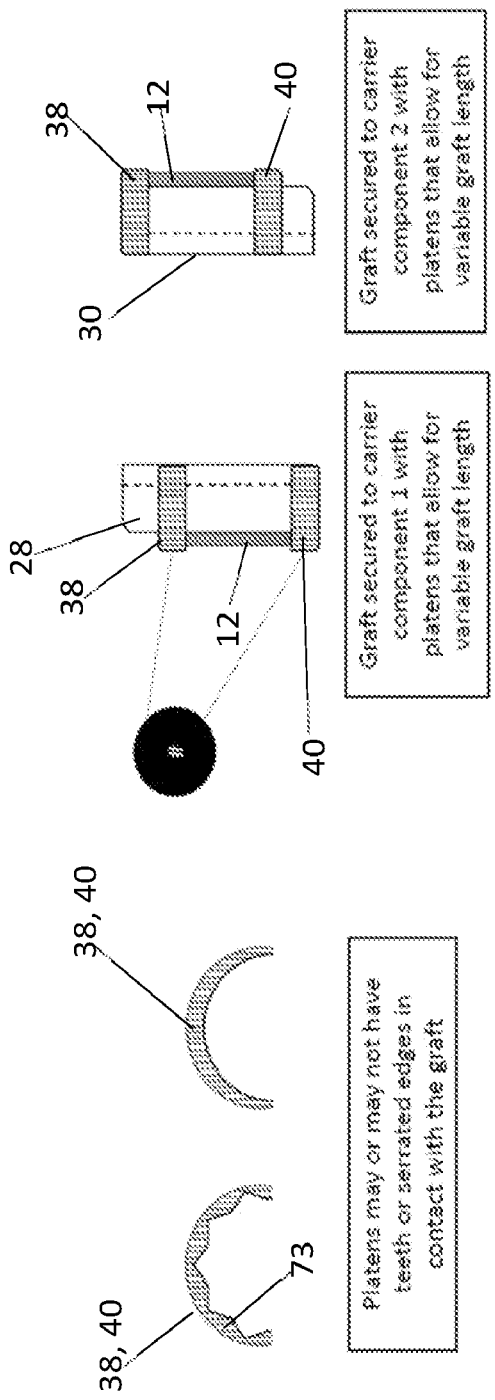

FIGS. 22 and 23A-23D illustrate side views of graft securement components, according to embodiments of the present invention. FIG. 22 illustrates a graft membrane 12 secured onto a carrier component 14 using platens 38, 40. The carrier component 14 can take the form of a single part or multiple parts, as described herein. FIGS. 23A and 23B illustrate views of platens 38, 40, according to an embodiment of the present invention. The platens 38, 40 can include a texture element 73, such as teeth or serrated edges that are in contact with a surface of the graft membrane. FIG. 23C illustrates a graft membrane 12 secured to a carrier component 14 with platens 38, 40 that allow for variable graft length. FIG. 23D illustrates a graft membrane 12 secured to a carrier component 14 with platens 38, 40 that allow for variable graft length. As illustrated in FIGS. 22 and 23A-23D the graft membrane 12 is secured onto one or more carrier component parts with platens of various sizes and configurations. Securing the graft membrane 12 in this way allows for various graft sizes.

Figure 24:
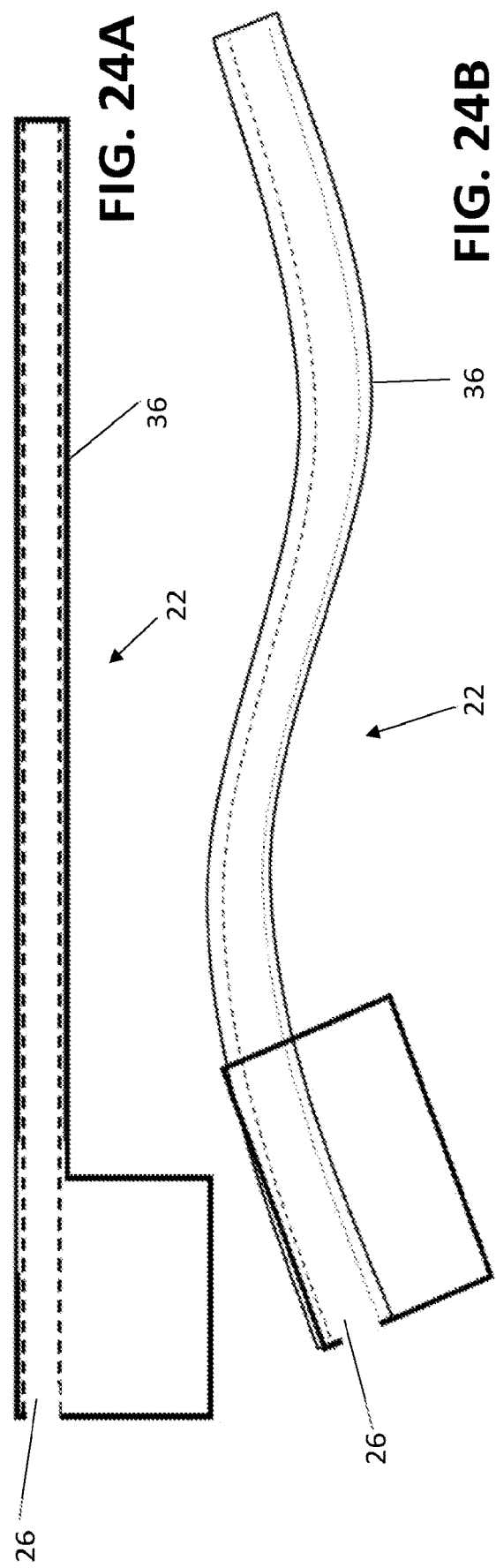
FIGS. 24A and 24B illustrate side views of delivery components according to an embodiment of the present invention.
Figure 25:
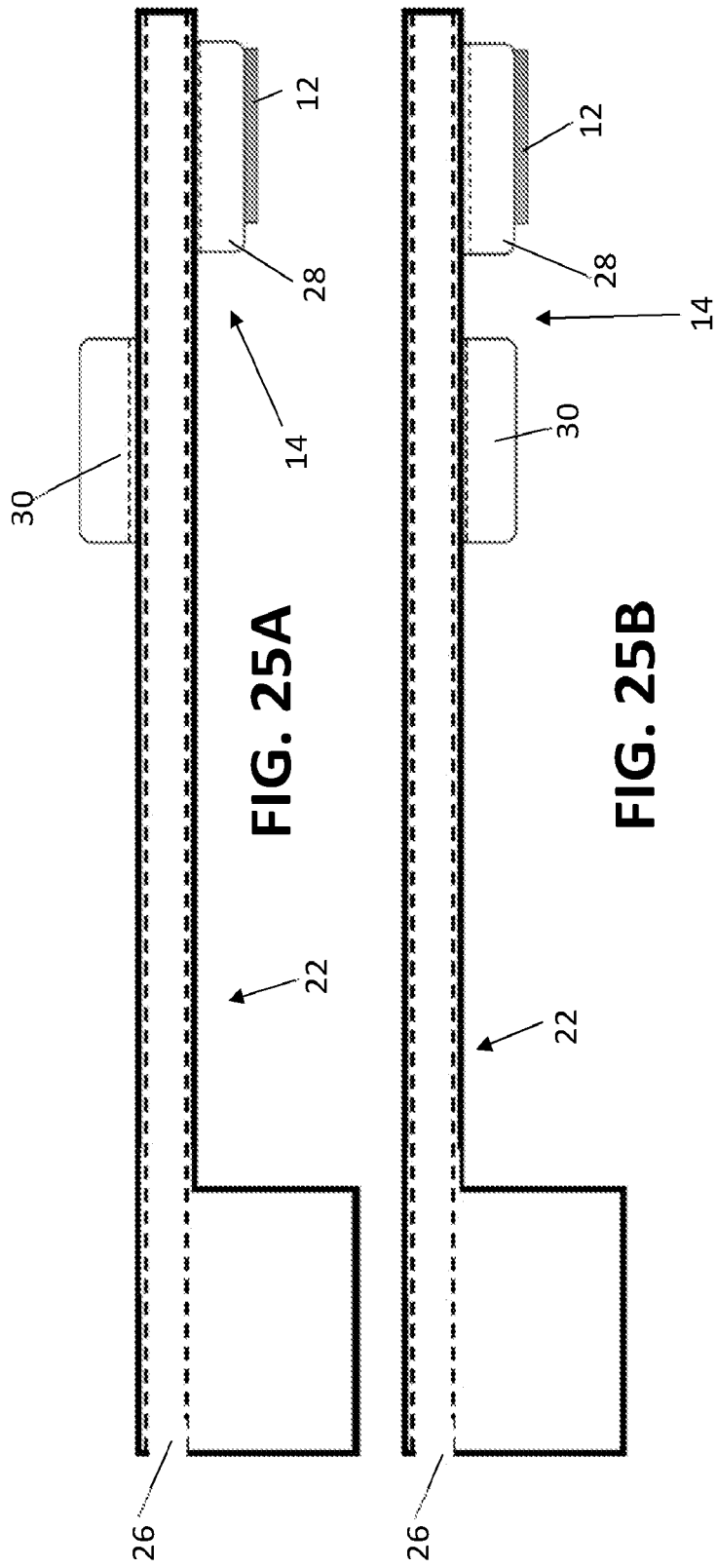
FIGS. 25A and 25B illustrate side views of carrier component positioning on the delivery component for delivery into the urethra, according to embodiments of the present invention.

FIGS. 24A and 24B illustrate side views of delivery components according to an embodiment of the present invention. FIGS. 24A and 24B illustrate that the delivery component 22 may be rigid, solid, or flexible in nature. The delivery component 22 also may define an inner lumen that allows for the passage of accessories for visualization, illumination, stricture incision, and irrigation. FIGS. 25A and 25B illustrate side views of carrier component positioning on the delivery component for delivery into the urethra, according to embodiments of the present invention. FIG. 25A illustrates carrier component parts 28, 30 disposed in a serial opposite position on the delivery component 22 for delivery into the urethra. FIG. 25B illustrates carrier component parts 28, 30 in a serially in-line position on the delivery component 22 for delivery into the urethra.

Figure 26:
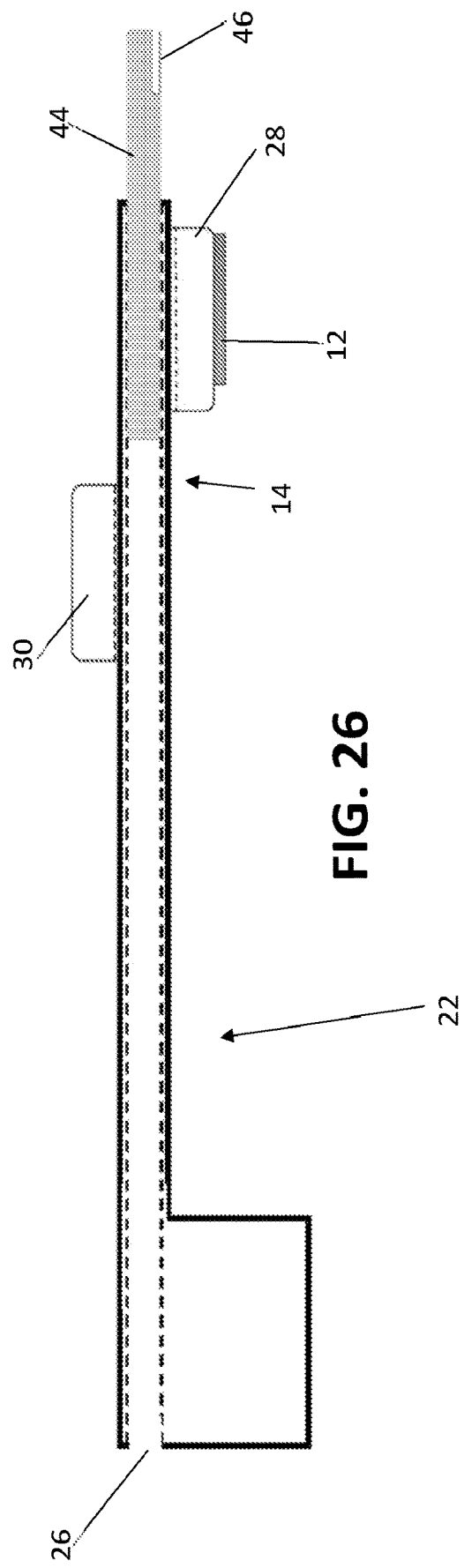
FIG. 26 illustrates a side, partially sectional view of an internal sheath according to an embodiment of the present invention.

FIG. 26 illustrates a side, partially sectional view of an internal sheath according to an embodiment of the present invention. An internal sheath 44 can extend through a lumen 26 defined by the delivery component 22 either completely or partially. An internal sheath 44 at a distal end 30 of the delivery component 22 can also include a slot 46 for passage of a cutting edge of a stricture incision tool. The internal sheath 44 can also be used for locking and unlocking of the carrier component pieces. To summarize, the graft carrier component can be disposed in serial or a serial offset within the delivery component. Alternately, the graft carrier component can be disposed in concentric parts, inscribed or nested, or jointed, hinged or interleaved. These possible configurations are not meant to be considered limiting, and it should be noted that any graft carrier component configuration known to or conceivable to one of skill in the art could be used. Fundamentally, the graft carrier component should hold the graft, provide for necrosis of graft tissue to facilitate removal of the graft carrier component after adherence, provide fixation of the graft within the urethra during adherence, and allow for a Foley catheter. The graft carrier components parts can be joined to reach expanded position by sliding, rotation, or joint/hinge actuation. A locking mechanism can also be engaged to hold the parts together in the desired configuration. The graft carrier component can also include surface features that prevent fluid accumulation, perforate the graft, and/or reduce movement of the graft carrier component within the urethra. A graft loading device can also be included. The graft is loaded on a loader component and rolled onto the graft carrier component. Lines or markers can be included to aid in positioning the graft. Fixation of the graft carrier component within the urethra can be achieved in a number of ways. Fixation can be pressure based, i.e. a lumen of the graft carrier component is expanded to expand the size of the graft carrier component. Surface characteristics such as pins, barbs, textures, hydrophobicity/hydrophilicity, or any combination of these can also be used. Barbs can include furcations and can in some instances be bioresorbable. Sutures are another option for fixation of the graft carrier component. Any other method of fixation known to or conceivable by one of skill in the art can also be used.

Figure 27A:
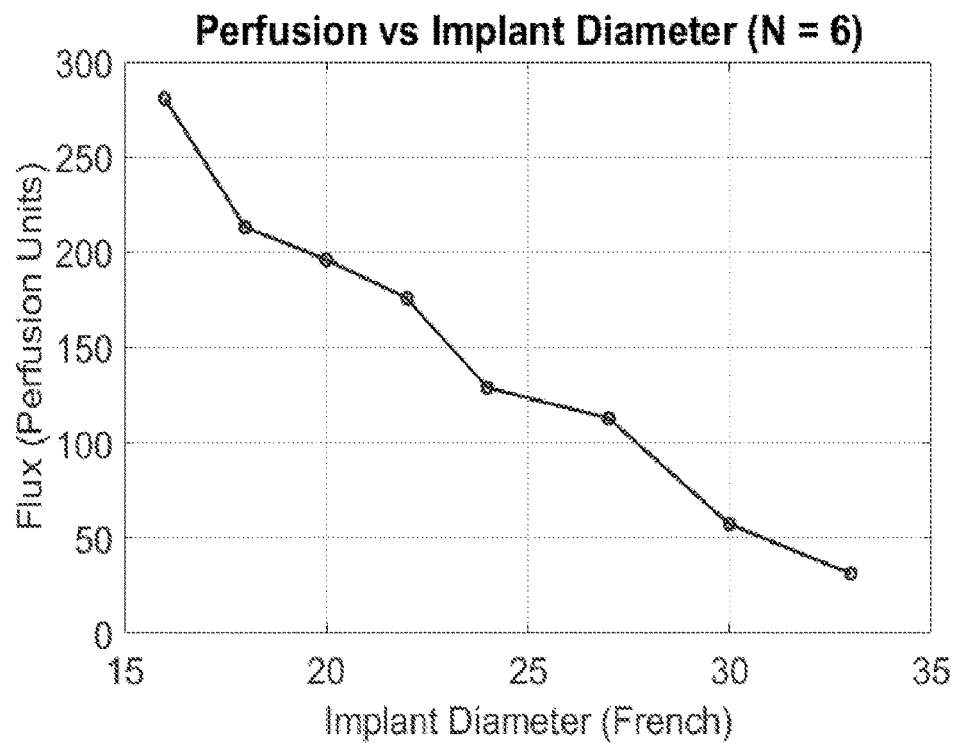
FIGS. 27A-27D illustrate graphical views showing perfusion data, associated with an embodiment of the present invention.
Figure 27B:
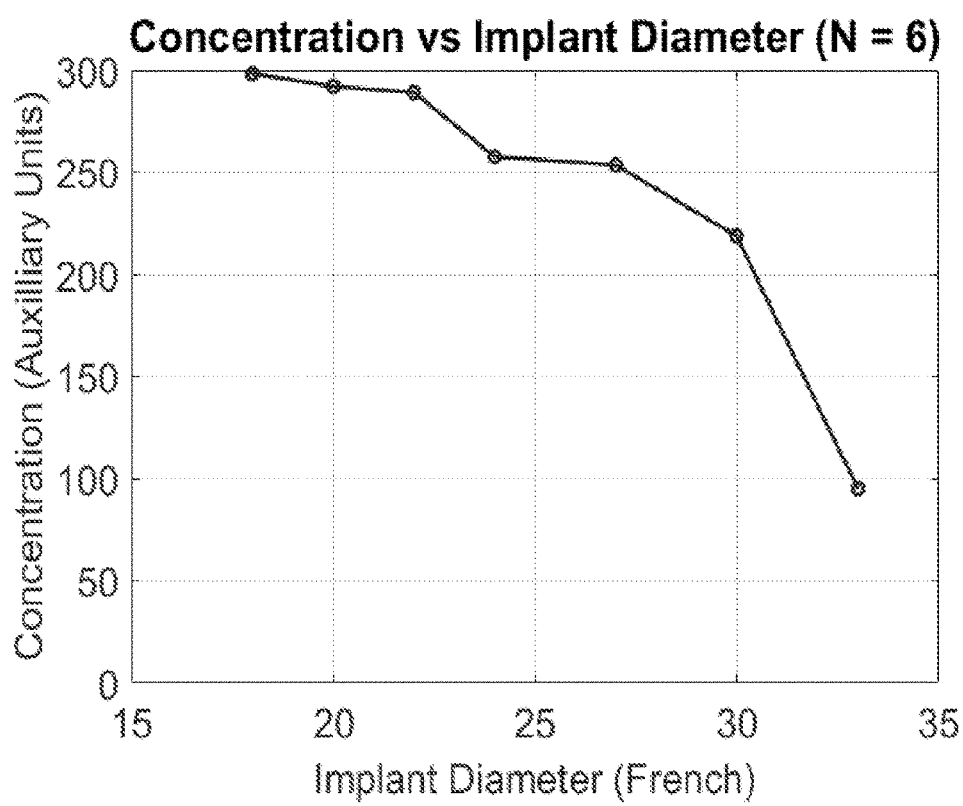
Figure 27C:
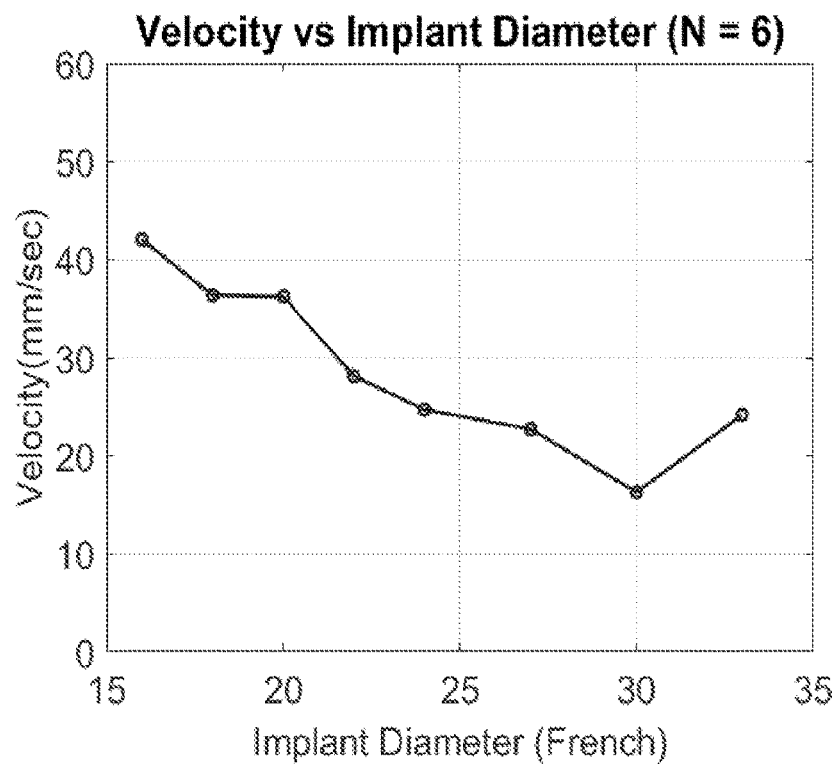
Figure 27D:
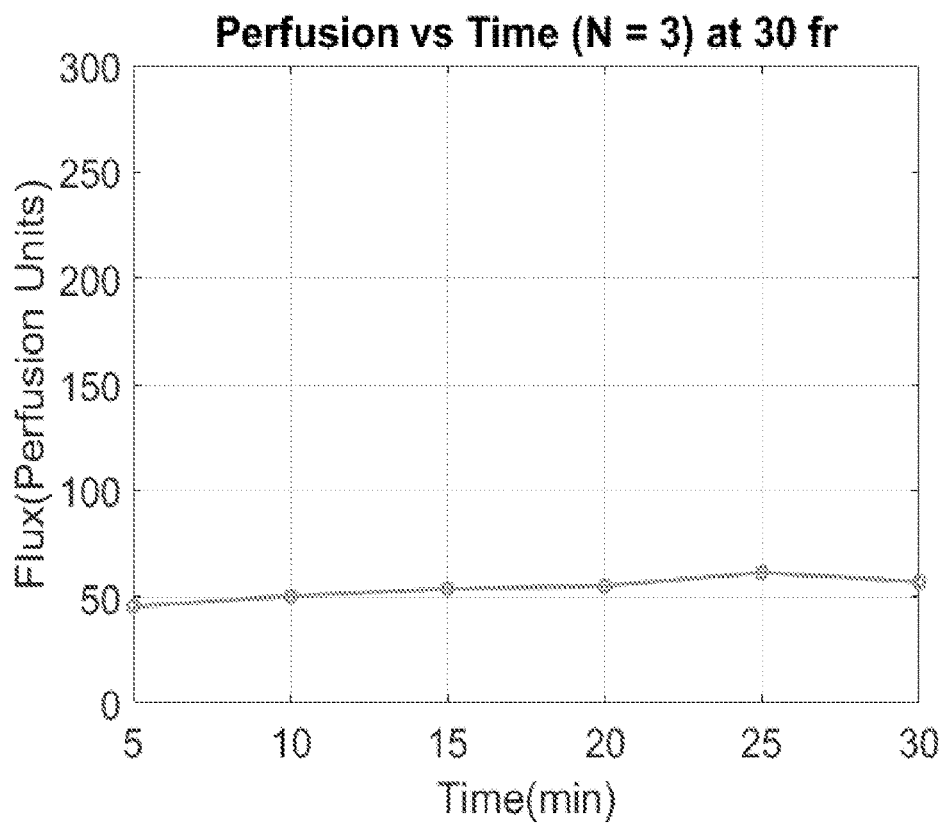

FIGS. 27A-27D illustrate graphical views showing perfusion data, associated with an embodiment of the present invention. All data was collected in 6 rabbits using laser Doppler flowmetry. FIGS. 27A-27D show a urethral expansion from 16 F-33 F, with 16 F, 18 F, 20 F, 22 F, 24 F, 27 F, 30 F and 33 F diameters tested. FIG. 27A illustrates perfusion versus implant diameter, with an overall decrease in perfusion from 16 F to 33 F. FIG. 27B illustrates concentration versus implant diameter, with an overall decrease in concentration from 16 F to 33 F. FIG. 27C illustrates velocity versus implant diameter, with an overall decrease in velocity from 16 F to 33 F. FIG. 27D illustrates perfusion versus time with minimal/little change in perfusion as a function of time.

The novelties stated herein facilitate the placement of a membrane in a lumen. While many possible embodiments and applications exist from outlined novelties, the following specific examples describe applications to perform a minimally invasive treatment for urethral stricture disease, for strictures located in the bulbar area of the urethra, with a length 4 cm or less; however, it can be utilized for strictures with all areas of the urethra and for all lengths. The procedure that incorporates the device can be done in 4 main steps. The first step is transurethrally incising the stricture. Next, a variable sized membrane is obtained (example: graft is harvested from the inside of the cheek or from the hairless region of the penis, with an approximate size of 1.5×4 cm, length (4 cm here) may vary depending on the length of the stricture). The device may come in embodiments of varying lengths.

An aspect of this disclosure involves a method of placing a membrane onto the device and securely attaching it. Embodiments of this device include using a platen/clamp that holds the edges of the graft; in some embodiments the platen/clamp also perforate the edges of the graft. Some embodiments use pins from the device that poke through the graft to secure it in place. Some embodiments use surface characteristics such as textured nubs, which pass through perforations in a fenestrated graft. Some embodiments include a separate tool for loading the graft onto the device. When using some potential embodiments of this disclosure, a device encompassing sheath may be inserted into the lumen until reaching the desired site. The device will then be passed through the sheath, until the site is reached. The device encompassing sheath will then be pulled back to allow the carrier component and graft to come in contact with the incised area, as the lumen collapses onto the device.

One possible embodiment uses pressure fixation alone. The graft is fixed to a primary half cylinder carrier (tapered at the ends), with a secondary tapered half cylinder in series behind the first. The graft is delivered transurethrally to be in contact with the incised area of the urethra. The delivery mechanism then rotates the second tapered cylinder 180 degrees, and pushes it forward so that it sits above the primary tapered cylinder, where they connect together. The carrier may be textured provide increased friction to be able to limit translational movement in the urethra in response to externally applied forces. Textures include depressed lines, wavy lines, cones, squares/rectangles, cylinders, ellipsoids, or other raised/depressed shapes. It may also have holes, grooves and/or channels to allow for the flow of exudate away from the site of stricture. Another exemplary embodiment uses pressure fixation in combination with mechanical pin fixation. At the time that the sheath is removed, a balloon offset from the center of the device is inflated to push the device in contact with the incised area. Once the device is in place, two hooks are pulled back, which causes a set of pins to be inserted across the graft into the corpus spongiosum. These pins are at an appropriate length so to firmly insert into the urethra without significantly damaging the tissue, and can help limit longitudinal motion within the urethra. For both example devices, the device will remain in place in the lumen for a range of 5-21 days before being removed. Materials used in the manufacture of these devices will be standard biocompatible materials used in device manufacture including but are not limited to: thermoplastics such as silicones, PDMS, PEBAX, PTFE, PEEK, polyurethane, nylon, stainless steel, titanium, and shape memory alloys such as nitinol.

Display of visual images or data related to the device and procedure of the present invention can be carried out using a computer, non-transitory computer readable medium, or alternately a computing device or non-transitory computer readable medium incorporated into the robotic device or the imaging device.

A non-transitory computer readable medium is understood to mean any article of manufacture that can be read by a computer. Such non-transitory computer readable media includes, but is not limited to, magnetic media, such as a floppy disk, flexible disk, hard disk, reel-to-reel tape, cartridge tape, cassette tape or cards, optical media such as CD-ROM, writable compact disc, magneto-optical media in disc, tape or card form, and paper media, such as punched cards and paper tape. The computing device can be a special computer designed specifically for this purpose. The computing device can be unique to the present invention and designed specifically to carry out the method of the present invention. The computing device can also take the form of an operating console computer. The operating console is a non-generic computer specifically designed by the manufacturer. It is not a standard business or personal computer that can be purchased at a local store. Additionally, the console computer can carry out communications with the scanner through the execution of proprietary custom built software that is designed and written by the manufacturer for the computer hardware to specifically operate the hardware.

The many features and advantages of the invention are apparent from the detailed specification, and thus, it is intended by the appended claims to cover all such features and advantages of the invention which fall within the true spirit and scope of the invention. Further, since numerous modifications and variations will readily occur to those skilled in the art, it is not desired to limit the invention to the exact construction and operation illustrated and described, and accordingly, all suitable modifications and equivalents may be resorted to, falling within the scope of the invention.

What is claimed is:
1. A device, comprising:
a membrane carrier component comprising at least two separate parts each configured to expand when placed at a urethral stricture site of a urethra,
wherein the at least two separate parts comprise a first part and a second part,
wherein the membrane carrier component expands by the first part and the second part moving away from each other on at least one side,
wherein the first part is configured to hold a membrane for placement at the urethral stricture site,
wherein the second part is configured to be in direct contact with the urethra and is associated with fixation of the membrane carrier component at the urethral stricture site, and wherein the membrane carrier component is configured to be fixated at the urethral stricture site by surface characteristics along a length of the second part; and a delivery component configured to secure at least one of the first part or the second part and deliver the membrane carrier component through the urethra to the urethral stricture site for the membrane to adhere to the urethral stricture site, wherein the first part and the second part move away from each other in a direction perpendicular to the delivery component during expansion.

2. The device of claim 1, wherein the at least two separate parts are positioned in at least one of: serial, serial offset, concentric, inscribed, nested, jointed, hinged, or interleaved.

3. The device of claim 1, wherein the at least two separate parts of the membrane carrier component comprise a locking mechanism for joining the at least two separate parts into a single part.

4. The device of claim 1, further comprising:
platens to hold the membrane in place on the membrane carrier component.

5. The device of claim 1, further comprising:
a fixation component for fixing the membrane carrier component at the urethral stricture site.

6. The device of claim 1, further comprising:
an endoscope for insertion through a lumen of the delivery component to allow for illumination and visualization of the urethral stricture site during incision of the urethral stricture site.

7. The device of claim 1, further comprising:
a tool for incising the urethral stricture site.

8. The device of claim 1, wherein the delivery component further comprises an elongate shaft,
wherein the elongate shaft defines a lumen, and
wherein the elongate shaft is configured to allow passage of the membrane carrier component.

9. The device of claim 1, further comprising:
an inner sheath for insertion into a lumen of the delivery component.

10. The device of claim 1, further comprising:
an external sheath defining a lumen configured to receive at least the delivery component.

11. A method, comprising:
securing a membrane to a first part of a carrier component, wherein the carrier component comprises at least two separate parts including the first part and a second part;
coupling at least one of the first part or the second part to a delivery component;
inserting, based on the coupling of at least one of the first part or the second part to the delivery component, the delivery component with the carrier component into a urethra;
advancing, based on the inserting of the delivery component with the carrier component into the urethra, the carrier component to a stricture site;
expanding the carrier component by the first part and the second part moving away from each other on at least one side,
wherein the second part is in direct contact with the urethra and is associated with fixation of the carrier component at the stricture site,
wherein the first part and the second part move away from each other in a direction perpendicular to the delivery component, and wherein the carrier component is fixated at the stricture site by surface characteristics along a length of the second part.

12. The method of claim 11, further comprising:
locking the at least two separate parts of the carrier component together.

13. The method of claim 11, further comprising:
inserting an incision tool through a lumen defined by the delivery component; and
incising the stricture site.

14. The method of claim 11, further comprising:
inserting an endoscope for illumination and visualization through a lumen defined by the delivery component.

15. The method of claim 11, further comprising:
fixing the carrier component at the stricture site.

16. The method of claim 11, further comprising:
passing a Foley catheter through a lumen defined by at least the carrier component.

17. The method of claim 11, further comprising:
leaving the carrier component at the stricture site for approximately 5-21 days.

18. The method of claim 11, further comprising:
removing the carrier component after membrane adherence at the stricture site.

19. A device, comprising:
a carrier component comprising at least two separate parts each configured to expand when placed at a site within a lumen,
wherein the at least two separate parts comprise a first part and a second part,
wherein the carrier component expands by the first part and the second part moving away from each other on at least one side,
wherein the first part is configured to hold a membrane for placement at the lumen,
wherein the second part is configured to be in direct contact with the lumen, and
wherein the carrier component is configured to be fixated at the site within the lumen by surface characteristics along a length of the second part; and
a delivery component configured to secure the at least one of the first part or the second part and deliver the carrier component through the lumen to the site within the lumen for treatment material contact at the site within the lumen,
wherein the first part and the second part move away from each other in a direction perpendicular to the delivery component during expansion.

20. The device of claim 19, wherein the delivery component is structured for the carrier component to be coupled to a fixed location on the delivery component during delivery.

21. The device of claim 19, wherein the carrier component expands based on movement associated with at least a first end of the first part and at least a second end of the second part.

22. The device of claim 19, wherein the expansion of the first part and the second part is achieved by actuation of the delivery component.

23. The device of claim 22, wherein the delivery component comprises inter-leaved components.

24. The device of claim 19, wherein the second part comprises a fixation component, and
wherein the carrier component is fixated at the site by the fixation component.

* * * * *